US011032986B2

(12) United States Patent
Chomet et al.

(10) Patent No.: US 11,032,986 B2
(45) Date of Patent: Jun. 15, 2021

(54) METHODS OF CREATING DROUGHT TOLERANT CORN PLANTS USING MARKERS LINKED TO COLD SHOCK DOMAIN-CONTAINING PROTEINS AND COMPOSITIONS THEREOF

(71) Applicant: MONSANTO TECHNOLOGY LLC, St. Louis, MO (US)

(72) Inventors: Paul S. Chomet, Mystic, CT (US); Nancy M. Houmard, St. Louis, MO (US); Hongwu Jia, Apex, NC (US); Michael R. Kerns, St. Louis, MO (US); Mark E. Leibman, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 16/445,041

(22) Filed: Jun. 18, 2019

(65) Prior Publication Data
US 2020/0015444 A1 Jan. 16, 2020

Related U.S. Application Data

(62) Division of application No. 14/072,081, filed on Nov. 5, 2013, now Pat. No. 10,383,295.

(60) Provisional application No. 61/723,378, filed on Nov. 7, 2012.

(51) Int. Cl.
C12Q 1/68 (2018.01)
A01H 5/10 (2018.01)
C12N 15/82 (2006.01)

(52) U.S. Cl.
CPC ........... A01H 5/10 (2013.01); C12N 15/8273 (2013.01)

(58) Field of Classification Search
None
See application file for complete search history.

(56) References Cited

U.S. PATENT DOCUMENTS

| 7,786,353 | B2 | 8/2010 | Fernandes |
| 2005/0097640 | A1 | 5/2005 | Fernandes |
| 2009/0100544 | A1 | 4/2009 | Anstrom et al. |

OTHER PUBLICATIONS

Zea mays cultivar B73 chromosome 10 clone ZMMBBb-472J14, GenBank accession No. AC201879, published on Sep. 23, 2013, selected pages.*
Civardi et al., 1994, The relationship between genetic and physical distances in the cloned al-h2 interval of the Zea mays L. genome, Proc. Natl. Acad. Sci. USA 91: 8268-8271.*
Castiglioni et al., "Bacterial RNA chaperones confer abiotic stress tolerance in plants and improved grain yield in maize under water-limited conditions," Plant Physiol 147:446-455, 2008.
Chaikam et al., "Comparison of structure, function and regulation of plant cold shock domain proteins to bacterial and animal cold shock domain proteins," BMB Reports 43(1):1-8, 2010.
Chaikam et al., "Functional characterization of two cold shock domain proteins from Oryza sativa," Plant Cell Environ 31(7):995-1006, 2008.
Guerra-Peraza et al., "ZmCOI6.1, a novel, alternatively spliced maize gene, whose transcript level changes under anbiotic stress," Plant Sci 176:783-791, 2009.
Harrigan et al., "The forage and grain of MON 87460, a drought-tolerant corn hybrid, are compositionally equivalent to that of conventional corn," J Agric Food Chem 57:9754-9763, 2009.
Kang et al., "Variance component model to account for sample structure in genome-wide association studies," Nat Genet 42(4):348-356, 2010.
Karlson et al., "A cold-regulated nucleic acid-binding protein of winter wheat shares a domain with bacterial cold shock proteins," J Biol Chem 277(38):35248-35256, 2002.
Karlson et al., "Conservation of the cold shock domain protein family in plants," Plant Physiol 131:12-15, 2003.
Lee et al., "Expanding the genetic map of maize with the intermated B73 x Mo17 (IBM) population," Plant Molec Biol 48:453-461, 2002.
Price et al., "Principal components analysis corrects for stratification in genome-wide association studies," Nat Genet 38(8):904-909, 2006.
Qin et al., "Regulation and functional analysis of ZmDREB2A in response to drought and heat stresses in Zea maize L," Plant J 50:54-69, 2007.
Yang et al., "Narrowing down the targets: Towards successful genetic engineering of drought-tolerant crops," Molec Plant 3(3):469-490, 2010.
Civardi et al., Proc. Natl. Acad. Sci. USA 91:8268-8271 (1994).

(Continued)

Primary Examiner — Bratislav Stankovic
(74) Attorney, Agent, or Firm — Dentons US LLP; Lawrence Lavin

(57) ABSTRACT

The present invention is in the field of plant breeding and drought tolerance. More specifically, the invention includes a method for breeding corn plants containing one or more markers that are associated with tolerance to low water conditions. Markers provided herein include markers genetically linked to proteins comprising cold shock domains, such as the CSD1 and CSD2 proteins. The invention further includes germplasm and the use of germplasm containing at least one marker associated with drought tolerance for introgression into elite germplasm in a breeding program, thus producing drought resistant germplasm. Other embodiments of this invention include transgenic drought tolerant corn plants and corn plant cells, and methods of detecting drought tolerance genes and chromosome regions associated with drought tolerance in a plant genome.

16 Claims, No Drawings
Specification includes a Sequence Listing.

(56) References Cited

OTHER PUBLICATIONS

Maize GDB Locus lim471a Record p. 651652, IBM2 2008 database, pp. 1-20.
Batley et al., In; Association Mapping in Plants, pp. 95-102 (2007).

* cited by examiner

SEQUENCE LISTING

```
<160> NUMBER OF SEQ ID NOS: 80

<210> SEQ ID NO 1
<211> LENGTH: 3160
<212> TYPE: DNA
<213> ORGANISM: Zea mays
<220> FEATURE:
<221> NAME/KEY: misc_feature
<222> LOCATION: (409)..(409)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (466)..(466)
<223> OTHER INFORMATION: n is a, c, g, or t
<220> FEATURE:
<221> NAME/KEY: misc_feature
<222> LOCATION: (504)..(506)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (763)..(763)
<223> OTHER INFORMATION: n is a, c, g, or t
<220> FEATURE:
<221> NAME/KEY: misc_feature
<222> LOCATION: (947)..(947)
```

```
<223> OTHER INFORMATION: n is a, c, g, or t
<220> FEATURE:
<221> NAME/KEY: misc_feature
<222> LOCATION: (955)..(956)
<223> OTHER INFORMATION: n is a, c, g, or t
<220> FEATURE:
<221> NAME/KEY: misc_feature
<222> LOCATION: (958)..(958)
<223> OTHER INFORMATION: n is a, c, g, or t
<220> FEATURE:
<221> NAME/KEY: misc_feature
<222> LOCATION: (967)..(967)
<223> OTHER INFORMATION: n is a, c, g, or t
<220> FEATURE:
<221> NAME/KEY: misc_feature
<222> LOCATION: (1076)..(1076)
<223> OTHER INFORMATION: n is a, c, g, or t
<220> FEATURE:
<221> NAME/KEY: misc_feature
<222> LOCATION: (1325)..(1325)
<223> OTHER INFORMATION: n is a, c, g, or t
<220> FEATURE:
<221> NAME/KEY: misc_feature
<222> LOCATION: (2818)..(2818)
<223> OTHER INFORMATION: n is a, c, g, or t
<220> FEATURE:
<221> NAME/KEY: misc_feature
<222> LOCATION: (2857)..(2857)
<223> OTHER INFORMATION: n is a, c, g, or t
<220> FEATURE:
<221> NAME/KEY: misc_feature
<222> LOCATION: (2895)..(2895)
<223> OTHER INFORMATION: n is a, c, g, or t
<220> FEATURE:
<221> NAME/KEY: misc_feature
<222> LOCATION: (2955)..(2955)
<223> OTHER INFORMATION: n is a, c, g, or t

<400> SEQUENCE: 1
tttctgtgat tgttttgtcc acaagaattc gcttctcaac tacttagtca cactaacatt      60
tctataacca agttttgtgg ctatttagtg ttgaattta caggatcacc tattcacccc     120
cctctaggtg ctctcaaaaa gggcatgccc cggtggtcac atggtgctat cccaaagac     180 cacactttaa tttgtgtctt ttccgaaaca catcacaccc tagagacatc ataatgtatg     240
ccaccctagg ccctaggaga gaatgaccct ttagcgcaca ctactcccct agttcttgtc     300
atgactatga tgatgcaacc tctaagtatg aaggttcctc ccaaccatga ttattccagc     360
aggctcgtta accatgatgc aacctctaag tatgaatgcc ttaactttng caccaacgat     420
aactttagca ccaacgatgt tgtagtcccc ctcggcacnt ataagnccttt ctctataaca     480 ctctaacatc tcataccata aaannngagt gctgagcaat agtgacttga tgtcgttagg     540
tttatagcca ctgccaaggt taaccctaga tcctctcaac tcgtgcattc tcgttgcagc     600
tagccacgcc gcgacaacct cgtgctcttg ttccctaaca atggtttctc tagggtctag     660
ccatgagggt cgtaccccag gttcaatatg agcaccaaca tgcccgactc cttgacccgc     720
tcntttcaat actctgtata ctttaagagc atctccaaca atncctcaaa tcaatgcact     780
atctcgaaat atagggccaa actcataaaa aacagctcca caatgttttt tacaattttc     840
tatcaaaata tgctacacat catattagtg gtctatcctt gtttatgtac catcctaaca     900
ttttctttcc taataatgta atttactttc taaaatacat gatttcnggc ttaanngntg     960
aagctcnatt tgttttagt gccctaatca ctctaaaaga tgtactttct ctgttcttaa    1020
atatttgtcg ccctctagtt tattttcaca ctaaactgcg acaaaaaga ggaagngagt    1080 agtattttaa ttttggttc acattattga agatgctcta atattttaa aataactaat    1140 tttttatgta tatgtaaacg ttagatatag tgtatatcta aatatttata atttactttc    1200
```

```
gagacaagat agacattggg ctcctttcta aatctgtagt atctcgtttc aagaaatcac    1260
cgtcaaatca aatcaaatct aatgtaacaa atatatggaa ataaatattt tttatttcta    1320
taatnttatt atactcaatc aaataatgaa gttttagagt aagagtatat tttctttctg    1380
ttgacacgac aaacaacatg ctactgataa agaatcacag aaaccatagt aacacagcaa    1440
gtagtactac tcgagtagta taaaaaaaat agacaacatg gagttcacca atcacgagga    1500
ggagcacgag ggccattcac gcccgtgtat accggatcga accgtgtcca ttgccaccgg    1560
ccccacccgt cataaagcac agaaaaccaa cccaaccaac agcgccgctg cctgccatcc    1620
cctcccccga cctcccctgc catgctggcc cacgccacac gtgagactcc caaccagggc    1680
ccacctcgcc ctaggtgctg gtgcttctgc cgctgccgac cacaccgcat ccgaccctcc    1740
gcccacgtct ccagagccat ctcggccgtc cgatcctccc gcgccttcct cgtatgcgcc    1800
gccctcctct atataaagta cgcgttggca cgaagcgagc agataagatc gagcagcgag    1860
agacgggcag gggagaggga aaaaaaaatc taaccctagc atccgcagcg ctagggttcg    1920
ggggttgcga tggcggcggc ggcgagacag cggggggacgg tgaagtggtt caacgacacc    1980
aagggcttcg ggttcatctc ccccgaggac ggcagcgaag atctcttcgt gcaccagtcg    2040
tcgatcaagt cggagggctt ccgctcgctc gcggagggcg aggaggtgga gttttccgtc    2100
tcggagggtg acgacggccg cactaaggcc gtcgacgtga ccggcccga cggatccttc    2160 gtcaggggcg gcggaggcgg aggaggaggc ggcggcggct acggctcccg cggcggtggc    2220
ggatctggcg gcggcggtcg cagctacggt ggtagctggg gcggcggccg gagatccggc    2280
ggcggggcgg gtcccggcgc gtgctacaag tgcggcgagc ccggccacat ggcaagggac    2340
tgccctagcg ccgacggcgg aggcggctac ggcggaggcg gctacggcgg cggcggctac    2400
ggaggaggag gcggcggcgg cggtggctgc ttcaagtgtg gcgagcctgg ccacatggcc    2460
agggactgct ccagcggcgg cggcggctac ggcggtggcg gcggcggcgg tggaggcggc    2520
tgctacaact gcggccaggc cggccacatg gccagggact gcccagcgg tggcggcggt    2580 ggcggaggga ggttcggcgg cggcggcggg ggtggcggcg accgctcctg ctacaactgc    2640
ggcgaggccg gccacatcgc ccgcgactgc cccacgtgag gtgtgtccgc gtccgtccgt    2700
ccagccagat cagatcggat cgctccacca cctgctggtc tgatggcgcc gccccttct    2760 agatctcgct taaaaaacac ccccctctcg ctgtgtgtcg gagtaccgct ttagttttngc    2820 cgatccgggc acgagtgccc gctgcctctt tcctctnatg cgtaagagga tcccgtccgc    2880
cgttttcaga tttcnttcgg ttcgtagaag aactctcaag ttaagttaag ttatcatggt    2940
gtgtgcttgg tcgtngttcg tcgtcgtcgt taaggtttta agagatgatt tggtcctgtg    3000
ttgccgaggg gaagtcgaat ctgctttttt ctttttttgt ggtttgttcc accagactga    3060
ggaaggagat gagatgatta ttctcccaga ttataatcct gcctgcttgt gcttgatttg    3120
gttaccacat atgccttcac cactaccgct cgatttgatt                         3160
```

<210> SEQ ID NO 2  
<211> LENGTH: 4320  
<212> TYPE: DNA  
<213> ORGANISM: Zea mays  
<220> FEATURE:  
<221> NAME/KEY: misc_feature  
<222> LOCATION: (3648)..(3648)  
<223> OTHER INFORMATION: n is a, c, g, or t  
<220> FEATURE:  
<221> NAME/KEY: misc_feature  
<222> LOCATION: (3728)..(3729)

```
<223> OTHER INFORMATION: n is a, c, g, or t
<220> FEATURE:
<221> NAME/KEY: misc_feature
<222> LOCATION: (3756)..(3756)
<223> OTHER INFORMATION: n is a, c, g, or t
<220> FEATURE:
<221> NAME/KEY: misc_feature
<222> LOCATION: (3763)..(3763)
<223> OTHER INFORMATION: n is a, c, g, or t
<220> FEATURE:
<221> NAME/KEY: misc_feature
<222> LOCATION: (3776)..(3776)
<223> OTHER INFORMATION: n is a, c, g, or t
<220> FEATURE:
<221> NAME/KEY: misc_feature
<222> LOCATION: (3799)..(3799)
<223> OTHER INFORMATION: n is a, c, g, or t
<220> FEATURE:
<221> NAME/KEY: misc_feature
<222> LOCATION: (3815)..(3815)
<223> OTHER INFORMATION: n is a, c, g, or t
<220> FEATURE:
<221> NAME/KEY: misc_feature
<222> LOCATION: (3849)..(3849)
<223> OTHER INFORMATION: n is a, c, g, or t
<220> FEATURE:
<221> NAME/KEY: misc_feature
<222> LOCATION: (3852)..(3852)
<223> OTHER INFORMATION: n is a, c, g, or t
<220> FEATURE:
<221> NAME/KEY: misc_feature
<222> LOCATION: (3860)..(3863)
<223> OTHER INFORMATION: n is a, c, g, or t
<220> FEATURE:
<221> NAME/KEY: misc_feature
<222> LOCATION: (3869)..(3869)
<223> OTHER INFORMATION: n is a, c, g, or t
<220> FEATURE:
<221> NAME/KEY: misc_feature
<222> LOCATION: (3880)..(3881)
<223> OTHER INFORMATION: n is a, c, g, or t
<220> FEATURE:
<221> NAME/KEY: misc_feature
<222> LOCATION: (3926)..(3926)
<223> OTHER INFORMATION: n is a, c, g, or t
<220> FEATURE:
<221> NAME/KEY: misc_feature
<222> LOCATION: (3932)..(3932)
<223> OTHER INFORMATION: n is a, c, g, or t

<400> SEQUENCE: 2
ttgtaacaaa gttgaactgc aaaaggtaaa acagacaatc accacagacc accaactctc      60
agaagacaag aatcagttta cttgccaaac ggttttaaaa atgattctga ttttctagga     120
gaatcaggag atcagctcc tcatgaggat caggatctgg agctaaagaa gcaggagctg      180
gagctttgcc aaacagtccc taaatcacca aaatacttag aaatgaccta aaggcacatt    240 tcccttcag taaacaagtc actaaatatg aatttaacaa gttttcgaga aaaaactctt     300
ctccaacagt tatgtaaatc agttccctaa atttacaaac tccctacaaa actcaatttc    360
atccctacat ttgccaacct ttttgggact tcttaaatca acgttggtac taatccacca    420
tgaaaaatca caattttgcc attgttttgc gttgtcccat tgtcctgttg accataaatc    480
catctccagc gcccaaatgt cttgatgccg tcactgctag ataacctctt atgccgagac    540
gtaatcagag cacatcctgt gatgtcttca cgccatcacc gtgaccgtct ggtctttcat    600
cgataacttc gacttctgaa gacatcaggg aaggttgtcg atattgattt ctacagtcag    660
ctcaattaaa aataggaagc atactcgctt attttttttgt tgacgtagac aactttcaaa   720
attagcaacc aataaatagg gaattgttga agcacataca tttttatact ccttaaagtg    780
ttttagcaac ttcttaaatt tataatttag agtgctaaat ttacataact attggagatg    840
```

| | | | | | |
|---|---|---|---|---|---|
| ctcttagctt | agctaggaca | atgggccggt | tgccagcggc | tataggaaat | gggaattgag | 900 |
| gatggggaa | tgtgtgagtg | cgtgacagtg | aaggaggctg | agagccagag | acggtgtcta | 960 |
| gggtttttca | atgagactag | ctaaatgggc | ttgggacagt | tgggctgtag | tgggctataa | 1020 |
| gtctacaata | ttttggtcaa | aactgtgtga | ctatcatcta | taatattata | atgtactggg | 1080 |
| tttaacaaac | acatgggttc | atgggtatga | gtactaatat | ctcatgctcg | tacccgtgta | 1140 |
| ccagttgggt | ttagattatc | acccattaag | aaacccgtgg | gtttagatat | tagcccatac | 1200 |
| ccgtccccta | atagagtaaa | aacccgtcgg | gtttcgggta | gcgggtaccc | attgccatct | 1260 |
| ctagacaagt | gacacggtga | ttttcgtacc | gtagttcggt | caagcgtaat | atgcttgcct | 1320 |
| agtccacgtt | gtggtgtcac | aatggacgag | ggttacactc | aacctctttc | aagtgatcca | 1380 |
| aagattaaac | ttgagtacca | caattttgtt | ctttatatca | aatccctcaa | gcgaggaatc | 1440 |
| tccatatttt | ggagtctctc | acgccttaca | caactgttct | ccaataaaca | caagagtaaa | 1500 |
| agggggaagt | ttctacaaat | attccaaaag | taaatttaag | atgtaagatt | aatagtttta | 1560 |
| ttttataaca | attagaatcg | gatagtatcc | actccatggt | aaaataaatg | ttaataatac | 1620 |
| atttatttca | tattaataca | tctgtctttt | ttagcttttg | agtttctgtc | tatgtgcaaa | 1680 |
| tagatgatta | tttttctgtt | tatgctcaaa | tagttgatga | taaatctaaa | cacataaata | 1740 |
| aaacgaatac | attaattatt | gtatgaatta | atttgaaagt | taaaacgaat | tttatttgaa | 1800 |
| ttggacgttt | tgtcgtatat | tcacaaagaa | atatgtgcag | tcgcgggctg | cgagggcggg | 1860 |
| gtctggtcac | ggagccggtc | aaggtgcagt | caagcagcga | cgaggggagg | caggcggtca | 1920 |
| gagactcaga | gcgcgcagaa | gaagctggcg | aatcagggcg | gctagttgga | cttgacgact | 1980 |
| tgtcacgtcc | cgtgcgtgcc | gaacttgccg | tgcgcagcaa | cctacctacc | ccggcccacc | 2040 |
| gttgcggtcc | cgtgcatgcg | cagccgggtt | ccgctcccgc | ggtcaccggc | gccggccccg | 2100 |
| gccccgcctt | ccgtttcagt | gctcttcggc | tttcacgcac | cggggcgcgc | gcggttgcat | 2160 |
| ttgcgtgcgc | cgctggtacc | cgaccgtgcc | cggtgagtcg | gtgaccgcgg | tgaagacttc | 2220 |
| cgaggctctc | gtggtagcac | gacatatgtt | tcagcgaccc | gactaggcct | gtgcgtggcg | 2280 |
| cgacgcgttc | cgatgcatgg | tccaagcctg | cctgtttcaa | gcatttgtta | cagtgaacga | 2340 |
| gttatcaacc | agatgttttg | ctgaccggat | aaggaatttt | tgttattttt | ttacaaatgt | 2400 |
| taaattaaaa | caagaaacaa | aatattcatg | ttttttcggt | ttgttactac | gctaaattaa | 2460 |
| atcaagaaac | aaaagctcgt | caaattagga | agcaaaaaaa | aaatcaaata | ctaggcggca | 2520 |
| atctaaggta | ggaagccaaa | tccggccttt | cttcctctcg | gaaatactt | aaaaggccct | 2580 |
| tgttccttgt | acccgctgaa | gataagaccc | actaaaaaca | cgacccacat | gtcagtggaa | 2640 |
| tttcaaaacg | ctgccagttc | catccccatt | ccgaccctgc | cgccgcaccc | accccaaccc | 2700 |
| caacccaacg | ggccgggtcc | cttcagattc | tcgacagtcc | gcgttaaata | ggccgccccg | 2760 |
| ctcgccttcc | actcctcgtt | cccacacccc | tcaccgcgtc | cgcctcccct | accatctagg | 2820 |
| gtttctaggg | ttttcgagga | ggaggaaatg | gcgtctgata | gggtgctcgg | gactgtgaag | 2880 |
| tggttcaacg | gaaccaaggg | cttcggtttc | atcaccccg | acgacggtag | cgaggaccta | 2940 |
| ttcgtccacc | agtcctccat | caagtccgac | ggctaccgca | gtcttaacga | cggcgatgcc | 3000 |
| gtcgaataca | ccgtcggcag | cggcaacgac | ggccgcgcca | aggccctcga | tgtcaccgcg | 3060 |
| cccggcggcg | gcccgcttgc | cggcggggaa | cgtcccgacg | gcggcaacgg | cggtgggcga | 3120 |
| ggcggatacg | gcggcggcga | ccgcggttac | ggcggcggcg | gtgaccgcgg | ctacggggga | 3180 |

```
ggaggcgacc gtggctacgg cggcggcgac cgtggttacg gtggaggtgg cgaccgcggc    3240
tacggcggcg accgtggcta cgggggaggc ggcggctatg gcgtgggta cggtggaggc    3300 ggcggtggag gcggccgcgg ctgcttcaag tgcggcgagg agggccacat ggcaagggac    3360
tgctcccagg gcggcggcta cggaggggga ggcggcggcg gccgcggcag cgagtgctac    3420
aactgcggcc aggagggcca catctcccgc gactgcccca caaaaggcg ttaggcggcg    3480 gcgccaccgt cgcgtcggat ccggcggaat cccatgttgg ctctcccgg ttttctttcc    3540 cctctaaaaa ggtatcgctc ggctgactct tgcgtgaagt cgtcggagca aactatctat    3600
cagtagtact agcagtgtcg tttcgttttg gtctgtcgcg gcgtggtngt aagaaatgca    3660
agtgagcagc accagtatgt ttccgtttga atcagttgta aggcagtcaa aaccatggta    3720
actctgcnng atctatctgt catgaactat ctatantata tcnttatcaa tgttangcaa    3780
tgagtctttg gcattgagnt aaggtaaaat actgnaatgc ctttgttgat tcttttggtt    3840
ggttttcgnt cntgtgtcgn nnntaatcnt tgcaggatcn ncttcggcgt ccttttgtg    3900 ttaaattatg atagcggagt gggatngttg tnttaagatc cttttgtgtt gtattatgat    3960
agtgcatagt ggagtgagac tgggtctcaa agagatgggg aaattactac tatgacgaaa    4020
attcgagttc atcagaataa aggatgaaat gtattgggg gagaaggagc cgaaaggtga    4080
agagtggtca gatggatggt gtattggtgc ggtaaagtgt gctgcaaaag caagcaggca    4140
ccaggtgcag tgctgctgct gtgcagactg gcactggcat tgctgttttg gcaacagaga    4200
gcgtctgggt ctgggtggca tggtatgggt ctgcttcatg cacgagcacg gcgccaggct    4260
ctgttttgtc cgcatcgcgg ggcggttgtg gaaaagcgag gggcggtttc catttctgtt    4320
```

<210> SEQ ID NO 3
<211> LENGTH: 1078
<212> TYPE: DNA
<213> ORGANISM: Zea mays
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (371)..(372)
<223> OTHER INFORMATION: n is a, c, g, or t
<220> FEATURE:
<221> NAME/KEY: misc_feature
<222> LOCATION: (392)..(392)
<223> OTHER INFORMATION: n is a, c, g, or t

<400> SEQUENCE: 3

```
caggttgtac tggccagctg gtgcaatgta acttattttc cccatagaac ccggtggaag      60
agcaacatgg tgctgcatca atgtgttctc aaaaacagtc tgcaacacac acccagtccg     120
caatcattag gatgtaaaca cgggttaaca gnatgcattt acatatcaca gacagctagt     180
cttcagaatg aagccataga tggaagtcaa tgtcataaga acttacagcg tatagatctc     240
cacctgtgat gacatctcca acacctggaa atatagcaca agaaaaccta tttagatagc     300
atcaaagttc aaatacaact tagagataac aaaaacagca tgcaaaacca tttcaacaat     360
ggaggtacta nnttaagtca ctacctagct tngttggctg aaattcccac aatacatctt     420
tgtcaagggc aggaactgaa acaccacgag gaatatacac atctcctgac ttaatagcga     480
tggtttttag aggtcgctgc aaacataata gagggcgagt gaggataata gacaaaaaat     540
aatgtaaatg gccgcaaaag taagcccgt cgtgttcagc acacctggat accgtcaaaa     600
atgtttccaa gaattccagg tcccaattca actgaaagag gctgcatggg aatagccatt     660
```

```
acatgttaaa tgatagcaaa agaatgatat taaaagatat agtaagatct gaagacaact      720
aaaacaaacc tttcttgttc tcaatacagg gtcattaacc atcagtccag ctgtttcctc      780
ataaactgca acacgcaaat gacggcactc gcgaggttag taccgtgtat tcaactggaa      840
aggagctttt catgcccatg ggtgaataat ttattataga tgatctgcca tgttgcatac     900
cttggattgt agctgaatcg ccctcaagac ggataatttc cccaatgagg ttatcatgtc      960
cgacacgaac aagttcatac atggcagcac cacccattcc atcagccaca accacaggtc     1020
cagagacctg caataaccca gcatcaaggc taatcaaagt ggggcttgtt atatacat       1078
```

```
<210> SEQ ID NO 4
<211> LENGTH: 661
<212> TYPE: DNA
<213> ORGANISM: Zea mays
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (209)..(209)
<223> OTHER INFORMATION: n is a, c, g, or t

<400> SEQUENCE: 4
```

```
taccectgac agcaaagaac aatgcatgct attaaatctg ttagatggtt cagaaatttc       60
tgagaaacac aaaataggtt ctgcatagaa ctgaacgtga agacagggac aaaccgcagt      120
gagaacccgg tccttctgta caagattaag aatgaaccca gcctccttac tgttatttgc     180
ttcagtagaa tcatctctgc ctacnatant agttgtaagc atagactttc catagatcac      240
agtttcaaga atcaagtgtg acatgacatg gaaacgtgca ccatcatcaa gttgcccata      300
ctgggatctt acccttagta aggacctgca gcaataagtt actaaactgt caaattaacc      360
atcatcaagc gaatgattat atataaaata agattacaaa tcctaccaaa tcaagaaatg      420
cagtctattt ttgcactgat catcttcaga gataatatta gggagcagtg atataaattg      480
ctgaacacat ttggatgcgt tttctaagcc agctttgcag agatacataa tgatgagatg     540
gaagataatt cttggaaatc tctcccctct tagcatcata gctttgtcag caactttgtt     600
agtctttcca cctaatgcgc tactgatgcc tcctgttaca actacagcag ccatttctgc    660
a                                                                      661
```

```
<210> SEQ ID NO 5
<211> LENGTH: 1157
<212> TYPE: DNA
<213> ORGANISM: Zea mays
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (415)..(415)
```

```
<223> OTHER INFORMATION: n is a, c, g, or t
<220> FEATURE:
<221> NAME/KEY: misc_feature
<222> LOCATION: (482)..(485)
<223> OTHER INFORMATION: n is a, c, g, or t
<220> FEATURE:
<221> NAME/KEY: misc_feature
<222> LOCATION: (506)..(507)
<223> OTHER INFORMATION: n is a, c, g, or t
<220> FEATURE:
<221> NAME/KEY: misc_feature
<222> LOCATION: (536)..(546)
<223> OTHER INFORMATION: n is a, c, g, or t
<220> FEATURE:
<221> NAME/KEY: misc_feature
<222> LOCATION: (555)..(559)
<223> OTHER INFORMATION: n is a, c, g, or t
<220> FEATURE:
<221> NAME/KEY: misc_feature
<222> LOCATION: (561)..(570)
<223> OTHER INFORMATION: n is a, c, g, or t
<220> FEATURE:
<221> NAME/KEY: misc_feature
<222> LOCATION: (593)..(597)
<223> OTHER INFORMATION: n is a, c, g, or t
<220> FEATURE:
<221> NAME/KEY: misc_feature
<222> LOCATION: (630)..(631)
<223> OTHER INFORMATION: n is a, c, g, or t
<220> FEATURE:
<221> NAME/KEY: misc_feature
<222> LOCATION: (635)..(635)
<223> OTHER INFORMATION: n is a, c, g, or t
<220> FEATURE:
<221> NAME/KEY: misc_feature
<222> LOCATION: (637)..(637)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (644)..(653)
<223> OTHER INFORMATION: n is a, c, g, or t
<220> FEATURE:
<221> NAME/KEY: misc_feature
<222> LOCATION: (659)..(661)
<223> OTHER INFORMATION: n is a, c, g, or t
<220> FEATURE:
<221> NAME/KEY: misc_feature
<222> LOCATION: (663)..(675)
<223> OTHER INFORMATION: n is a, c, g, or t
<220> FEATURE:
<221> NAME/KEY: misc_feature
<222> LOCATION: (678)..(695)
<223> OTHER INFORMATION: n is a, c, g, or t
<220> FEATURE:
<221> NAME/KEY: misc_feature
<222> LOCATION: (697)..(738)
<223> OTHER INFORMATION: n is a, c, g, or t
<220> FEATURE:
<221> NAME/KEY: misc_feature
<222> LOCATION: (755)..(761)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (779)..(784)
<223> OTHER INFORMATION: n is a, c, g, or t
<220> FEATURE:
<221> NAME/KEY: misc_feature
<222> LOCATION: (788)..(790)
<223> OTHER INFORMATION: n is a, c, g, or t
<220> FEATURE:
<221> NAME/KEY: misc_feature
```

```
<222> LOCATION: (792)..(798)
<223> OTHER INFORMATION: n is a, c, g, or t
<220> FEATURE:
<221> NAME/KEY: misc_feature
<222> LOCATION: (803)..(810)
<223> OTHER INFORMATION: n is a, c, g, or t
<220> FEATURE:
<221> NAME/KEY: misc_feature
<222> LOCATION: (816)..(822)
<223> OTHER INFORMATION: n is a, c, g, or t
<220> FEATURE:
<221> NAME/KEY: misc_feature
<222> LOCATION: (890)..(890)
<223> OTHER INFORMATION: n is a, c, g, or t
<220> FEATURE:
<221> NAME/KEY: misc_feature
<222> LOCATION: (975)..(1014)
<223> OTHER INFORMATION: n is a, c, g, or t

<400> SEQUENCE: 5
aacagcaaag taacagaaat caggaacata ccattacaaa caccatcaca tgtctcctgc      60
atttcgtcat aggttcctcg gtgcgattca ncttcganaa accaacgtag atccgtccgg     120
tccgatgcca ctgcacaatt caggtttaag ccttganaag tgaggacagt ttacccgtgc     180
gaaggcgtgc gattcaaggc cgctggtgag gaggtcagcg acgtccttct tgaggaactt     240
gaccatcgct tgcttcttcc gccgcagcag atccagccgg gtccgggtgc acttgatcgc     300
gtgcttgcta caccaaacag caactaaatc agcggttggg gtagtagaaa tcaaacaaat     360
acaggtgaca ggtcaaatcg agaatgcagg aatctggana acagcggga aagcngaaca     420
cagatcaaga acaggagcag gaacgctcgc aagtccgggg aacagttcct tggattcgca     480
gnnnnagatg agaagtggag ctaaannatt cggatcgagg gacgagcgga atgcgnnnnn     540
nnnnnnattc gcccnnnnnt nnnnnnnnnn aaacagaaaa gctgaacaga tcnnnnncga     600
aggaagctca aaacaatcga tttcgagctn nggtntncag anannnnnnn nnnaaaaann     660
nannnnnnnn nnnnngannn nnnnnnnnnn nnnnannnn nnnnnnnnnn nnnnnnnnnn     720
nnnnnnnnnn nnnnnnnta ccatttgttg tagannnnnn ngttgagcag actgtcnann     780
nnnntgcnnn gnnnnnnngg tgnnnnnnnn tccccnnnnn nncgcttctc tctgctccct     840
tctcttcggc tcttctccta cagctccgcc ctcggctttt agccagtggn agaggaggtg     900
gtgggaggca cgcagagcgg cagaggcaga ggcggggcgg ccaaagctgc tgcgagctgt     960
ggcgtcaaag catcnnnnnn nnnnnnnnnn nnnnnnnnnn nnnnnnnnnn nnnngtggtg    1020
gactggtggt ggtggtggcc tggtggagtg ggggaagatg gctgggtgga ggtagtggag    1080
aaggaaggaa aatatgagct gttgatgagg agaagccagg tggccatgac cagcaggtat    1140
cattctgctg catgcac                                                   1157

<210> SEQ ID NO 6
<211> LENGTH: 354
<212> TYPE: DNA
<213> ORGANISM: Zea mays
<220> FEATURE:
<221> NAME/KEY: misc_feature
<222> LOCATION: (231)..(231)
<223> OTHER INFORMATION: n is a, c, g, or t

<400> SEQUENCE: 6
atcattgggt gtggtggtta tggtctagtc tacaaggctg aactacctga tggctgcaag      60
cttgctatca agaagctcaa tgatgaaatg tgcttgatgg aaagggagtt cactgcagag     120
gttgaagcac tgtccatggc acagcacgac catcttgtgc cactgtgggg gtactgcatc     180
```

```
cagggggaact cgaggttcct catatactcc tacatggaga atggcagcct ngatgattgg      240
cttcacaaca gggatgatga tgccagcaca tttcttgact ggccgacgag gctaaggatt      300
gcgcaaggag caagccgtgg cctttcttat atccataatg actgcaaacc tcac           354
```

<210> SEQ ID NO 7
<211> LENGTH: 418
<212> TYPE: DNA
<213> ORGANISM: Zea mays
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (353)..(358)
<223> OTHER INFORMATION: n is a, c, g, or t
<220> FEATURE:
<221> NAME/KEY: misc_feature
<222> LOCATION: (378)..(383)
<223> OTHER INFORMATION: n is a, c, g, or t

<400> SEQUENCE: 7

```
aacgaaatac tagttgacat ggcagngtgt gctgccacca agctccagtg ccttagggta       60
tgttccttac catggctacc atgtgtagat agatagcatt tacaaatcga tggaatgcat      120
ggagctcctt agactagtga aaaaagaaa gccagagctg aaaggactgt aaaaaatgtt      180
cctgtaatng acatttcaag ctccgctgtt tattgttgta cttgtaatat tcatttgtgc      240
cttttgggat ctctcagcat ttgtcacggt acttcaaaca atctgctacg acaatggagc      300
aacagttcca aaaggagact aggttctaca gctccttaat aaggtagtta ctnnnnnnga      360
agttctaaat gtgaaagnnn nnnaaaaaac tgaagttctt gacccaattg ctgatgca       418
```

<210> SEQ ID NO 8
<211> LENGTH: 594
<212> TYPE: DNA
<213> ORGANISM: Zea mays
<220> FEATURE:
<221> NAME/KEY: misc_feature
<222> LOCATION: (100)..(100)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (369)..(371)
<223> OTHER INFORMATION: n is a, c, g, or t
<220> FEATURE:
<221> NAME/KEY: misc_feature
<222> LOCATION: (398)..(398)
<223> OTHER INFORMATION: n is a, c, g, or t
<220> FEATURE:
<221> NAME/KEY: misc_feature
<222> LOCATION: (474)..(475)
<223> OTHER INFORMATION: n is a, c, g, or t
<220> FEATURE:
<221> NAME/KEY: misc_feature
<222> LOCATION: (493)..(497)
<223> OTHER INFORMATION: n is a, c, g, or t
<220> FEATURE:
<221> NAME/KEY: misc_feature

```
<222> LOCATION: (515)..(519)
<223> OTHER INFORMATION: n is a, c, g, or t
<220> FEATURE:
<221> NAME/KEY: misc_feature
<222> LOCATION: (568)..(571)
<223> OTHER INFORMATION: n is a, c, g, or t
<220> FEATURE:
<221> NAME/KEY: misc_feature
<222> LOCATION: (575)..(589)
<223> OTHER INFORMATION: n is a, c, g, or t

<400> SEQUENCE: 8
gtaacagaag tcactgagct ggaagaatcg cctgggctct cagcctcagc cttggatgag      60
gaacccaacg cttgtgttca agcagtgctt ctcagggagn caaacncact aggacacaat     120
caaagaactg tagttcctag atcacagcat gcatctaatg tactggcntg gaaatgagtt     180
ggtgattgtt ggacctcgat atgctggttc tgtgccaccc attgcaacaa gaggtctgga     240
aaacagcaag gagagcggtg aaggggctt caaacccaaa ccttgtaaca acattttcca      300
aaatggctct tcaaagcctg aaagggaacc gggcaattcg tcaaacaaaa gaacagctgg     360
taaaacggnn naggaccttg gtcacaagga tagttcanct gaagtgtcct acgagtactg     420
tgtaagggtg gtcaggtggc tggagtgcga gggctacatc gagacaaact tcanngtgaa     480
gtttctcaca tgnnnnngcc tgcgtgccac cccgnnnnng agaaagatag tcggtgtcta     540
tgtggatacc cttattgagg accctgtnnn ncttnnnnnn nnnnnnnnng acag           594

<210> SEQ ID NO 9
<211> LENGTH: 674
<212> TYPE: DNA
<213> ORGANISM: Zea mays
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (247)..(247)
<223> OTHER INFORMATION: n is a, c, g, or t
<220> FEATURE:
<221> NAME/KEY: misc_feature
<222> LOCATION: (249)..(252)
<223> OTHER INFORMATION: n is a, c, g, or t
<220> FEATURE:
<221> NAME/KEY: misc_feature
<222> LOCATION: (255)..(258)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (376)..(376)
<223> OTHER INFORMATION: n is a, c, g, or t
<220> FEATURE:
```

<221> NAME/KEY: misc_feature
<222> LOCATION: (380)..(380)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (396)..(397)
<223> OTHER INFORMATION: n is a, c, g, or t
<220> FEATURE:
<221> NAME/KEY: misc_feature
<222> LOCATION: (618)..(619)
<223> OTHER INFORMATION: n is a, c, g, or t
<220> FEATURE:
<221> NAME/KEY: misc_feature
<222> LOCATION: (623)..(633)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (643)..(643)
<223> OTHER INFORMATION: n is a, c, g, or t
<220> FEATURE:
<221> NAME/KEY: misc_feature
<222> LOCATION: (646)..(649)
<223> OTHER INFORMATION: n is a, c, g, or t
<220> FEATURE:
<221> NAME/KEY: misc_feature
<222> LOCATION: (651)..(670)
<223> OTHER INFORMATION: n is a, c, g, or t

<400> SEQUENCE: 9

```
tggaccattt tgtttctttg atttagatac tgaagcatta ctgaatatat tcataagaca      60
angccatctg aaaacataac anggcctttg tttaaatttt gattttgacc atttcatatg     120
gaatattggt ttgatcacaa atacatgatc ttcncataac tcctctaaga atgtgatctt     180
cangtggaaa ctgctatcgc catgacntgg cagagattgt cgatcttcct tcagccatgc     240
ttggtgntnn nnagnnnnaa gcgacaaaca gaccaagttg ttcatccgat gtcgaagcca     300
gaggagtttc aggaaaatcg gcttatgttn atgttttatt gttatgtcat ggacgagtg      360
tgtatcagga taaatntagn aaaaaagaan tttttnnctt aaaatttggt catgtactca     420
attatttctt tgccgcagga atatcatgga gcatatgtgc tcttcctggt tgatggactg     480
gttctacctt tactgcctct gcctgagccc ccacctcatg cctggtccat ctccaggagt     540
tcactgtcca ccacggcatc tgtgcacatg gaaacgacca cctcgtgacc gatgtcttac     600
ttttacgatc aacactgnnt ccnnnnnnnn nnnctgatna ccnttnnnnc nnnnnnnnnn     660
nnnnnnnnnn ctca                                                      674
```

<210> SEQ ID NO 10
<211> LENGTH: 1273
<212> TYPE: DNA
<213> ORGANISM: Zea mays
<220> FEATURE:
<221> NAME/KEY: misc_feature
<222> LOCATION: (157)..(159)
<223> OTHER INFORMATION: n is a, c, g, or t
<220> FEATURE:
<221> NAME/KEY: misc_feature
<222> LOCATION: (178)..(180)
<223> OTHER INFORMATION: n is a, c, g, or t
<220> FEATURE:
<221> NAME/KEY: misc_feature
<222> LOCATION: (270)..(277)
<223> OTHER INFORMATION: n is a, c, g, or t -continued

```
<220> FEATURE:
<221> NAME/KEY: misc_feature
<222> LOCATION: (283)..(285)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (302)..(306)
<223> OTHER INFORMATION: n is a, c, g, or t
<220> FEATURE:
<221> NAME/KEY: misc_feature
<222> LOCATION: (311)..(313)
<223> OTHER INFORMATION: n is a, c, g, or t
<220> FEATURE:
<221> NAME/KEY: misc_feature
<222> LOCATION: (315)..(317)
<223> OTHER INFORMATION: n is a, c, g, or t
<220> FEATURE:
<221> NAME/KEY: misc_feature
<222> LOCATION: (319)..(323)
<223> OTHER INFORMATION: n is a, c, g, or t
<220> FEATURE:
<221> NAME/KEY: misc_feature
<222> LOCATION: (334)..(335)
<223> OTHER INFORMATION: n is a, c, g, or t
<220> FEATURE:
<221> NAME/KEY: misc_feature
<222> LOCATION: (337)..(338)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (350)..(362)
<223> OTHER INFORMATION: n is a, c, g, or t
<220> FEATURE:
<221> NAME/KEY: misc_feature
<222> LOCATION: (365)..(374)
<223> OTHER INFORMATION: n is a, c, g, or t
<220> FEATURE:
<221> NAME/KEY: misc_feature
<222> LOCATION: (379)..(395)
<223> OTHER INFORMATION: n is a, c, g, or t
<220> FEATURE:
<221> NAME/KEY: misc_feature
<222> LOCATION: (399)..(405)
<223> OTHER INFORMATION: n is a, c, g, or t
<220> FEATURE:
<221> NAME/KEY: misc_feature
<222> LOCATION: (411)..(425)
<223> OTHER INFORMATION: n is a, c, g, or t
<220> FEATURE:
<221> NAME/KEY: misc_feature
<222> LOCATION: (428)..(438)
<223> OTHER INFORMATION: n is a, c, g, or t
<220> FEATURE:
<221> NAME/KEY: misc_feature
<222> LOCATION: (440)..(440)
<223> OTHER INFORMATION: n is a, c, g, or t
<220> FEATURE:
<221> NAME/KEY: misc_feature
<222> LOCATION: (452)..(452)
<223> OTHER INFORMATION: n is a, c, g, or t
<220> FEATURE:
<221> NAME/KEY: misc_feature
<222> LOCATION: (455)..(582)
<223> OTHER INFORMATION: n is a, c, g, or t
<220> FEATURE:
<221> NAME/KEY: misc_feature
<222> LOCATION: (584)..(611)
<223> OTHER INFORMATION: n is a, c, g, or t
<220> FEATURE:
<221> NAME/KEY: misc_feature
<222> LOCATION: (620)..(632)
```

```
<223> OTHER INFORMATION: n is a, c, g, or t
<220> FEATURE:
<221> NAME/KEY: misc_feature
<222> LOCATION: (652)..(652)
<223> OTHER INFORMATION: n is a, c, g, or t
<220> FEATURE:
<221> NAME/KEY: misc_feature
<222> LOCATION: (657)..(659)
<223> OTHER INFORMATION: n is a, c, g, or t
<220> FEATURE:
<221> NAME/KEY: misc_feature
<222> LOCATION: (667)..(671)
<223> OTHER INFORMATION: n is a, c, g, or t
<220> FEATURE:
<221> NAME/KEY: misc_feature
<222> LOCATION: (675)..(677)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (806)..(808)
<223> OTHER INFORMATION: n is a, c, g, or t
<220> FEATURE:
<221> NAME/KEY: misc_feature
<222> LOCATION: (999)..(999)
<223> OTHER INFORMATION: n is a, c, g, or t

<400> SEQUENCE: 10
cagagcgttc taatttgctt cttcatatag taagcactag caaacttgtc catcaaatag      60
taactataca gaccagcatt acacaccttc acaactattt ctgctccgtc aaatgcaaga     120
gtagcaagcg acagcacctg atcgacatga tccatgnnna ctccagagta ccagttannn     180
aaaaaacgtc catagtagct gtcatagtcg cctccatcac aaaaaaagcc agtttcatgt     240
ggtcttgaat tataatagcc agcgttatcn nnnnnnngtg ccnnaacaa atgaccccgn      300 gnnnnngctg nnngnnntnn nnnctttgc atgnncnngt cataacantn nnnnnnnnn      360 nnatnnnnnn nnnnaatgnn nnnnnnnnnn nnnnatgnn nnnnctatc nnnnnnnnnn      420 nnnnnagnnn nnnnnnnngn ctagtaagcc angtnnnnnn nnnnnnnnnn nnnnnnnnnn      480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnannnnnnn nnnnnnnnnn     600
nnnnnnnnnn ngacagcagn nnnnnnnnnn nntgcttgac atgttgatgc ancaaannnc     660
atgtttnnnn nagannnatt atgacacaga tactgaatgc aaacagagct tgtttatgtc     720
cagatcgtaa gagtttaggt ggattccaaa gattactccc aaanaaancc cttgcaaatt     780
tcaacttggt atttaagtac tagtannnaa tacctgaaac tcaccaatac caggatattt     840
ccagcccatt gtttctggac atgaaggata tcttagctcc cctgaagcac ccaatccaat     900
ttcgatagaa gaaacaaggc cctcttcaga taagtttctg aattccatat ggaaactcct     960
catgaaatca aaacagacct gcagatgatc ttgttaagnc tcggtgtact agttttttc    1020 ttcatttata gtatggcatt caaacaaagc taggtagaag gtacactaaa gttaagtgtt    1080
tcaatacaag gaaatggtt ttgctatctt ctaaattaaa ttgtaggtac cacagtgcag     1140
aaagatggga aaatgacaat ctaagatcta accaaagtaa tataaggaga atggtgctcc    1200
tatttcttgt caaagatga agagaggaga aaatttacca agtgtgaccc aatacctcaa    1260
tgccagttct ccc                                                       1273
```

<210> SEQ ID NO 11
<211> LENGTH: 699
<212> TYPE: DNA
<213> ORGANISM: Zea mays
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (585)..(586)
<223> OTHER INFORMATION: n is a, c, g, or t
<220> FEATURE:
<221> NAME/KEY: misc_feature
<222> LOCATION: (590)..(591)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (610)..(613)
<223> OTHER INFORMATION: n is a, c, g, or t
<220> FEATURE:
<221> NAME/KEY: misc_feature
<222> LOCATION: (619)..(621)
<223> OTHER INFORMATION: n is a, c, g, or t
<220> FEATURE:
<221> NAME/KEY: misc_feature
<222> LOCATION: (647)..(648)
<223> OTHER INFORMATION: n is a, c, g, or t
<220> FEATURE:
<221> NAME/KEY: misc_feature
<222> LOCATION: (658)..(662)
<223> OTHER INFORMATION: n is a, c, g, or t
<220> FEATURE:
<221> NAME/KEY: misc_feature
<222> LOCATION: (678)..(678)
<223> OTHER INFORMATION: n is a, c, g, or t
<220> FEATURE:
<221> NAME/KEY: misc_feature
<222> LOCATION: (681)..(698)
<223> OTHER INFORMATION: n is a, c, g, or t

<400> SEQUENCE: 11

```
tggagagctg gtaggaccac agaggcagaa nggctgttag agaggatgag tgagaaagga    60
tacagtttgg atacggctgg ctgcaatatc attattgatg ggttatgcag gaatagtaaa   120
ttagatgtgg ctatgggcat tgttgatggg atgtgggaag aaggaagcac ngctcttggc   180
cgactgggga attcattcct tagtgtagtt agtgattctt ccatcagcca agatgtctt    240 cctgatcgga tcacatattc tattttgata agtgcattgt gcaaagaagg caggtttgat   300
gaagccaaga agaaattact tgagatgata gtgaaagata tttcccctga ttcagttata   360
tatgacacct tcatccacgg gtattgtaag catggaaaga catctttggc tattaaggtt   420
ctgagggaca tggaaaagaa aggttgcaac ccaagcacaa ggacatacaa cttgttgatt   480
cggggatttg aagaaaaaca taaatcagat ganatcatga aactgatgag tgaaatggag   540
gagaaagggg tttctcctaa tgtgctgacc tacaatagct tgatnnagtn nttttgtcaa   600
canggaatgn nnnacaagnn natgcccctt ttggatgaaa tgctacnnaa tgaattgnnn   660
```

```
nntaatataa cttctttnga nnnnnnnnnn nnnnnnnnt                              699
```

```
<210> SEQ ID NO 12
<211> LENGTH: 781
<212> TYPE: DNA
<213> ORGANISM: Zea mays
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (235)..(235)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (430)..(430)
<223> OTHER INFORMATION: n is a, c, g, or t
<220> FEATURE:
<221> NAME/KEY: misc_feature
<222> LOCATION: (657)..(657)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t

<400> SEQUENCE: 12
acacaaccan ngaacttaca acttccaaca gggtatgtgc atgttttgc atgaaacagc          60 aacagcaacc actttatctg acggaggtaa tgaatatttc tcttgacctg cccaaaccct        120
ccagttgtgg gntttggcac tgcaggatca acagaagcga gagtgccatt agaaagacac       180
caatctgatg aaaatggttg ctgtactcca tcttgtgaca ttattctttg acaanaatct       240
tcttgtactt gtttttcgag tgatgaatta gtagcnacag gagcctttc cattgtttgt       300 ggctgccatt gagaaagcag catttgctct gtctgtgatc ctttcagcac ataacttaca       360
gcatttgaac cgttatcaag ctgcggatta gagggcaaca attgctgaga accatgtgag       420
gcagaaggan gaaaattttg agagctagat agatgaccaa gcatctgccc tcctttaaca       480
ttgtcaagag catttctttg ctggtattga ccctggaagt ttggaaggtc agcaggatca       540
ctagcttgtg aagaaactag ttcagtgtgt ggcagagtcc cctgttctgg cagttgcatt       600
gaatggttgg aagccatttg agactgttta agggaattgt tccttaacat agcctgntga       660
tgctgtgaat ttggctgctg ntgatttata tgatactgat tttgaataaa ctgggaatta       720
ggttgcacct gatgctgcga cattgggtgc tggtgtagta gttgatcatg agtcagggt       780 a                                                                       781
```

```
<210> SEQ ID NO 13
<211> LENGTH: 470
<212> TYPE: DNA
<213> ORGANISM: Zea mays
<220> FEATURE:
<221> NAME/KEY: misc_feature
<222> LOCATION: (237)..(237)
<223> OTHER INFORMATION: n is a, c, g, or t

<400> SEQUENCE: 13
ctgtaattct attaaacaag gttttccctc tgtcttcaaa ttggatttgc taactgttta        60
```

```
tttctgtaca atgaagatcg tgaggtgacg caatcaacag taaagaggaa ggcaccaaca    120
agtcaacctg cacgcttgtc aaatggatat ggacctaaga acacaatgtc aactcaaagg    180
catgctgaag gtaaggtaaa ttccatgaga agggaggatt tctcgaatac agaaagngtt    240
gtttcacgtg acaatgagag gatgtatgaa agggttgttt cacgtgataa tgagaggatg    300
catagtattg caagaaatgg atccaaccag gcaagtacta gcaaaccac aatccaaaag     360 catccaagca ggggtcccat tgttaataag caaccttcca aggattcgaa tgatgcaact    420
ctgaggaaga gcagtgtagc ctcaaagcac catcccttag agattgacag               470
```

<210> SEQ ID NO 14
<211> LENGTH: 697
<212> TYPE: DNA
<213> ORGANISM: Zea mays
<220> FEATURE:
<221> NAME/KEY: misc_feature
<222> LOCATION: (253)..(253)
<223> OTHER INFORMATION: n is a, c, g, or t
<220> FEATURE:
<221> NAME/KEY: misc_feature
<222> LOCATION: (413)..(413)
<223> OTHER INFORMATION: n is a, c, g, or t
<220> FEATURE:
<221> NAME/KEY: misc_feature
<222> LOCATION: (594)..(595)
<223> OTHER INFORMATION: n is a, c, g, or t
<220> FEATURE:
<221> NAME/KEY: misc_feature
<222> LOCATION: (610)..(615)
<223> OTHER INFORMATION: n is a, c, g, or t
<220> FEATURE:
<221> NAME/KEY: misc_feature
<222> LOCATION: (626)..(626)
<223> OTHER INFORMATION: n is a, c, g, or t
<220> FEATURE:
<221> NAME/KEY: misc_feature
<222> LOCATION: (628)..(629)
<223> OTHER INFORMATION: n is a, c, g, or t
<220> FEATURE:
<221> NAME/KEY: misc_feature
<222> LOCATION: (631)..(632)
<223> OTHER INFORMATION: n is a, c, g, or t
<220> FEATURE:
<221> NAME/KEY: misc_feature
<222> LOCATION: (636)..(639)
<223> OTHER INFORMATION: n is a, c, g, or t
<220> FEATURE:
<221> NAME/KEY: misc_feature
<222> LOCATION: (641)..(641)
<223> OTHER INFORMATION: n is a, c, g, or t
<220> FEATURE:
<221> NAME/KEY: misc_feature
<222> LOCATION: (652)..(653)
<223> OTHER INFORMATION: n is a, c, g, or t
<220> FEATURE:
<221> NAME/KEY: misc_feature
<222> LOCATION: (659)..(659)
<223> OTHER INFORMATION: n is a, c, g, or t
<220> FEATURE:
<221> NAME/KEY: misc_feature
<222> LOCATION: (675)..(681)
<223> OTHER INFORMATION: n is a, c, g, or t
<220> FEATURE:
<221> NAME/KEY: misc_feature
<222> LOCATION: (683)..(691)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t

<400> SEQUENCE: 14

```
gaacatcatc actgacgtct gatacagcaa aatgcagcag ctggtggatg gctttgttgt    60
ttgcagttcc cctataggct agagccaatg catacatacc accataacgt aatatgggat   120
cttgatctct agtcatttgt tcaatcaagg tgtctgcttc ctcttccctg ccatatactg   180
tcaatgcaat tcccagtgac aaaccctga aagagaaaga gaactgtcag agtgtagttc   240
ttcagatcaa gtncataagc actgtagaac aatcaaacag caccaacctt ataatctttt   300
catgctgtgt atcatgtgca taagcaagca tctcactagc cttctcactg gcggtcccaa   360
ccatgagcaa gcccatgcca ataccagctg cctcaccagc aacagcactg tcngtgtaaa   420
ggacattctt tatgtcctca tatatttcct catctgcggt tcccaaagct gcaagcccaa   480
gccccaaaca tgcaccatgc tggatgacct gtatgacatt gggggttgga gttagcataa   540
tatgcatgaa atgaataaca aaataaaaga cagaaaataa acaataatca cctnngcact   600
ggagttgcgn nnnnnttcac ggaggnanng nntgannnnt ncaccatgat tnncatgant   660
caaacctagt gcgtnnnnnn nannnnnnnn ngnatat                            697

<210> SEQ ID NO 15
<211> LENGTH: 575
<212> TYPE: DNA
<213> ORGANISM: Zea mays
<220> FEATURE:
<221> NAME/KEY: misc_feature
<222> LOCATION: (231)..(231)
<223> OTHER INFORMATION: n is a, c, g, or t

<400> SEQUENCE: 15
catcccaatc gcctcccctt gttgccgttg tgaatagcca gctctacgcc gccgaccagt    60
cgacgaacgt ggtcaagaag taattcggct cgagcaacgc ctgggacgta gtgaagccac   120
tgcccgtcag agctgactcg tccaatggct ggggcctagc tttcaaggcc tgtggcgata   180
ggttgctggt gatcggaggc catagaggac ctcgtggcga ggtaatactg ntgcattcct   240
ggtgccccga aggcggggaa gactgggagg ttctgtcggt gaaggaacgc gcaggcgtct   300
tcgtttacaa ctgtgcaata atgggggtgct gagttacctt ttgctcctcg gtacatgccg   360
cagctggttt agcaaggcaa cgaccatttc ttgctgccat ttagctacct tttatagtga   420
cttgtaattc agaaatgacc tcccctcccc gaaatctcgc ggcgctctca aatgttgaat   480
gttttgtaga gagcatatat agagcattca gttaagttta cctggaacta ccctctctct   540 ctttttttttc tgttaaactc gttcacattt ttttc                             575

<210> SEQ ID NO 16
<211> LENGTH: 1220
<212> TYPE: DNA
<213> ORGANISM: Zea mays
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (173)..(173)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (233)..(233)
<223> OTHER INFORMATION: n is a, c, g, or t
<220> FEATURE:
<221> NAME/KEY: misc_feature
```

```
<222> LOCATION: (271)..(271)
<223> OTHER INFORMATION: n is a, c, g, or t
<220> FEATURE:
<221> NAME/KEY: misc_feature
<222> LOCATION: (275)..(275)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (328)..(328)
<223> OTHER INFORMATION: n is a, c, g, or t
<220> FEATURE:
<221> NAME/KEY: misc_feature
<222> LOCATION: (410)..(410)
<223> OTHER INFORMATION: n is a, c, g, or t
<220> FEATURE:
<221> NAME/KEY: misc_feature
<222> LOCATION: (417)..(427)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (656)..(656)
<223> OTHER INFORMATION: n is a, c, g, or t
<220> FEATURE:
<221> NAME/KEY: misc_feature
<222> LOCATION: (693)..(694)
<223> OTHER INFORMATION: n is a, c, g, or t
<220> FEATURE:
<221> NAME/KEY: misc_feature
<222> LOCATION: (749)..(749)
<223> OTHER INFORMATION: n is a, c, g, or t
<220> FEATURE:
<221> NAME/KEY: misc_feature
<222> LOCATION: (814)..(815)
<223> OTHER INFORMATION: n is a, c, g, or t
<220> FEATURE:
<221> NAME/KEY: misc_feature
<222> LOCATION: (869)..(869)
<223> OTHER INFORMATION: n is a, c, g, or t
<220> FEATURE:
<221> NAME/KEY: misc_feature
<222> LOCATION: (932)..(932)
<223> OTHER INFORMATION: n is a, c, g, or t
<220> FEATURE:
<221> NAME/KEY: misc_feature
<222> LOCATION: (971)..(971)
<223> OTHER INFORMATION: n is a, c, g, or t
<220> FEATURE:
<221> NAME/KEY: misc_feature
<222> LOCATION: (1006)..(1006)
<223> OTHER INFORMATION: n is a, c, g, or t
<220> FEATURE:
<221> NAME/KEY: misc_feature
<222> LOCATION: (1132)..(1132)
<223> OTHER INFORMATION: n is a, c, g, or t
<220> FEATURE:
<221> NAME/KEY: misc_feature
<222> LOCATION: (1183)..(1183)
<223> OTHER INFORMATION: n is a, c, g, or t
<220> FEATURE:
<221> NAME/KEY: misc_feature
<222> LOCATION: (1198)..(1200)
<223> OTHER INFORMATION: n is a, c, g, or t
<220> FEATURE:
<221> NAME/KEY: misc_feature
<222> LOCATION: (1203)..(1210)
<223> OTHER INFORMATION: n is a, c, g, or t

<400> SEQUENCE: 16
tttgggagct ggccttatga aaaggtggtt tgattatgcc attcgctccc ttagaatttt    60
```

```
tttaatatgg ttagaagtac actttttatt ggcttgtana ttctctctaa caatgcctgt    120
acaatatttc tcttctacta ctattaatat ctagaacaat aggggctgcc canactgtag    180
tgctttaaaa agaancaatt tcagagttat tttagaattt tgaaaaccat ttnattatta    240
tgaaagcaag ttattttaga acattcaaac ncaancaatg attttttttct gncatgaaaa    300 gttcattcat gttttgatga gttttttnaa tgcaaattaa ctttggatca acatagcaac    360
ttagcaagca atttattcta caactttttt gttctctttt atctgaactn tgaagtnnnn    420
nnnnnnngnc tgtgatgtgg aatagaaga gctcaccaag aacatgttgg ttaacctta    480 ttatgtagtt tcctcagttt attatttctt gatcccagtc cctcgaagag ctcacaaaga    540
tggcccataa tttctatgat gagactgcac tcccaaagct ggtaagcctt gttttagcta    600
ttttgttaat tttcttaaa attttgagtc acttatagca acattcgcta ctttanctat    660
cttgtcctga tttgttcttt aattacccta tannaaactc ttgttatggt acatgatgtt    720
gagttagttt acttaatagt atcagagtng tcattctcaa gcatatatga tcttgggatg    780
ttttattccc atagtactta attcattttt tttnncttgg aatacatttc gtacaggtgg    840
ctgatttcgc gtcccttgag ctttctccng tggatggaag aaccatgacc gatttcatgc    900
atacaagggg acttaatatg tcctctttag gncgtgtggt gggtgtaaat tttatgccta    960
aatgcttttc ntactatgtt tggacaaagt tgcataataa tctganattg tttctttata   1020
ttaatcaggt agagctagca gagaagctcc cacacatcca gtctatatgc attcatgaaa   1080
tggttattag atcctttaag cacatcgtcc gagctgttat tgctgctgtt gntgacatgc   1140
aaaatatttc tgcagctata gctgaaactc taaacatatt acntggatct cccagacnnn   1200
aannnnnnnn cacagatgcc                                               1220

<210> SEQ ID NO 17
<211> LENGTH: 526
<212> TYPE: DNA
<213> ORGANISM: Zea mays
<220> FEATURE:
<221> NAME/KEY: misc_feature
<222> LOCATION: (296)..(296)
<223> OTHER INFORMATION: n is a, c, g, or t

<400> SEQUENCE: 17
gcaagaacgt cttctactgg ttccagaacc acaaggcccg cgagcgccag aagcagaagc     60
gagctgccct cctcaccctc agcaccacca ccactgcttc cacgctgcta ccaccagctg    120
ctgaaaccaa ggtatataac tatatatgca ttgcagcagc ttgcgttatg tatatatgca    180
ttgcatgcat aaatttaaat gcagtgaaca gctagcagta tcatcatatg tacgtacgta    240
tgcatgcaat gcaggaggga gtggagacga aaaagaaga agcgtgtgaa gatgcntcga    300
gccgcaagcg gaggtgcagg acctgggaag atgtcgtcgt ccatggtggc ggcgacgatg    360
ccggtacgga ggtagctgac gactactaca ccgacgacga tgtgaccctg gagctcttcc    420
cgctgcgtcc tgatcagggg aaataaagct agctagctag ctagctaact aattaagtaa    480
ggcggacaag cgtacgtata tgcgtaaagt atatgcccga tccatg                   526

<210> SEQ ID NO 18
<211> LENGTH: 311
<212> TYPE: DNA
<213> ORGANISM: Zea mays
<220> FEATURE:
<221> NAME/KEY: misc_feature
<222> LOCATION: (4)..(4)
<223> OTHER INFORMATION: n is a, c, g, or t
```

<220> FEATURE:
<221> NAME/KEY: misc_feature
<222> LOCATION: (39)..(45)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (223)..(223)
<223> OTHER INFORMATION: n is a, c, g, or t

<400> SEQUENCE: 18

```
tttnaggact ctcttatagt cttatttcaa gttgactann nnnnntacag agaaagaggc    60
atacctgttg gaccagtgta tactgcaagc tgcctgtaca acaaccattg ggatcaaagc   120
tcaattgcat atcncaatcg ctcagctaaa ggcattggaa aaacaagtag aaagtctagc   180
agcttactca gttgcatatc ccaatcgctc agctaaaggc atnattccta gcatgctgaa   240
aagaaaaacc aatccctgca attttaatgt cacgtgaacc atgtcagcat taagttaaca   300
gggggggggg g                                                       311
```

<210> SEQ ID NO 19
<211> LENGTH: 442
<212> TYPE: DNA
<213> ORGANISM: Zea mays
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (433)..(439)
<223> OTHER INFORMATION: n is a, c, g, or t

<400> SEQUENCE: 19

```
tttctcttat ggagtaatcc cagatataac ctctccattt ttgacatctc tttgctcttt    60
caggagttgg tgaaatttac acatatacta actaacgttc attttttgcag gtggagaaca  120
tttcntttga tttgtcacaa tacaacaatg ccccaagctt ccactggcct gaaagcagca  180
gcaggtctca gctccactga gtaggcagca atgcaatcgt ggatgccttc caaatagact  240
aagttctgac agtcttgtaa gggcttgttc ggttattcct atcttctgtg gattagatga  300
gattggaaaa aaatatgaaa gattttgact tgaaagattt tgacttgttt gggattaaaa  360
cgcacccaat tccactcaat ctacatggat tgagagcaaa accaacaagc cctaatttgg  420
aaaaaaaaaa aannnnnnng gg                                            442
```

<210> SEQ ID NO 20
<211> LENGTH: 590
<212> TYPE: DNA
<213> ORGANISM: Zea mays
<220> FEATURE:
<221> NAME/KEY: misc_feature
<222> LOCATION: (247)..(247)
<223> OTHER INFORMATION: n is a, c, g, or t
<220> FEATURE:
<221> NAME/KEY: misc_feature
<222> LOCATION: (445)..(445)
<223> OTHER INFORMATION: n is a, c, g, or t
<220> FEATURE:
<221> NAME/KEY: misc_feature
<222> LOCATION: (452)..(452)
<223> OTHER INFORMATION: n is a, c, g, or t
<220> FEATURE:
<221> NAME/KEY: misc_feature
<222> LOCATION: (505)..(505)

-continued

<223> OTHER INFORMATION: n is a, c, g, or t

<400> SEQUENCE: 20

```
ctgttctgag catgatgggc tgttcagcac tgaactgctg catagacgga tggagaaaac    60
agcagaaacg ctgggtttag ctggtatcac aatggatagt gctgagcttc tgaatattgc   120
tctggacaag tacatgaaaa acctgattag gtcatctgtt gagttagtag gaggtagtgt   180
tcagagggat gcaaggaaag ggacaccaac ctacaagcag caagcctatg gaaagcagat   240
taatggngtc cggctgccaa accatgttca tatgcaatca gccagtggat caccaggagc   300
caagaatgag attggaatta accatttgat ctccatcaat gactttaagg tagccatgca   360
gctaaaccct caacatctcg gggagaactg gccagtcctt ctggagaaga tatgtctatg   420
ttcttcagag gaaaatgact gacanatggc anttttttac ttcacagcga agttttgtac   480
caatgtgctt actggtgccc atccnatgta catttgagct ggaagtggca agattgcagg   540
cacaacacaa aatatgcaca tgtggggtca aggcagaaat ctgctcaacg                590
```

<210> SEQ ID NO 21
<211> LENGTH: 24
<212> TYPE: DNA
<213> ORGANISM: Zea mays

<400> SEQUENCE: 21

```
ccgcaatcat taggatgtaa acac                                            24
```

<210> SEQ ID NO 22
<211> LENGTH: 25
<212> TYPE: DNA
<213> ORGANISM: Zea mays

<400> SEQUENCE: 22

```
gcctccttac tgttatttgc ttcag                                           25
```

<210> SEQ ID NO 23
<211> LENGTH: 22
<212> TYPE: DNA
<213> ORGANISM: Zea mays

<400> SEQUENCE: 23

```
gccactgcac aattcaggtt ta                                              22
```

<210> SEQ ID NO 24
<211> LENGTH: 20
<212> TYPE: DNA
<213> ORGANISM: Zea mays

<400> SEQUENCE: 24

```
cgaccatctt gtgccactgt                                                 20
```

<210> SEQ ID NO 25
<211> LENGTH: 23
<212> TYPE: DNA
<213> ORGANISM: Zea mays

<400> SEQUENCE: 25

```
gccagagctg aaaggactgt aaa                                             23
```

<210> SEQ ID NO 26
<211> LENGTH: 25
<212> TYPE: DNA
<213> ORGANISM: Zea mays

```
<400> SEQUENCE: 26
tgtagttcct agatcacagc atgca                                           25

<210> SEQ ID NO 27
<211> LENGTH: 26
<212> TYPE: DNA
<213> ORGANISM: Zea mays

<400> SEQUENCE: 27
tgaccatttc atatggaata ttggtt                                          26

<210> SEQ ID NO 28
<211> LENGTH: 24
<212> TYPE: DNA
<213> ORGANISM: Zea mays

<400> SEQUENCE: 28
aaaacagacc tgcagatgat cttg                                            24

<210> SEQ ID NO 29
<211> LENGTH: 21
<212> TYPE: DNA
<213> ORGANISM: Zea mays

<400> SEQUENCE: 29
gttgatggga tgtgggaaga a                                               21

<210> SEQ ID NO 30
<211> LENGTH: 20
<212> TYPE: DNA
<213> ORGANISM: Zea mays

<400> SEQUENCE: 30
tctcttgacc tgcccaaacc                                                 20

<210> SEQ ID NO 31
<211> LENGTH: 28
<212> TYPE: DNA
<213> ORGANISM: Zea mays

<400> SEQUENCE: 31
tgaaagagaa agagaactgt cagagtgt                                        28

<210> SEQ ID NO 32
<211> LENGTH: 20
<212> TYPE: DNA
<213> ORGANISM: Zea mays

<400> SEQUENCE: 32
ctgatttcgc gtcccttgag                                                 20

<210> SEQ ID NO 33
<211> LENGTH: 21
<212> TYPE: DNA
<213> ORGANISM: Zea mays

<400> SEQUENCE: 33
aggagggagt ggagacgaaa a                                               21

<210> SEQ ID NO 34
<211> LENGTH: 23
<212> TYPE: DNA
```

<213> ORGANISM: Zea mays

<400> SEQUENCE: 34
catatcccaa tcgctcagct aaa                                            23

<210> SEQ ID NO 35
<211> LENGTH: 20
<212> TYPE: DNA
<213> ORGANISM: Zea mays

<400> SEQUENCE: 35
gcagcaagcc tatggaaagc                                                20

<210> SEQ ID NO 36
<211> LENGTH: 26
<212> TYPE: DNA
<213> ORGANISM: Zea mays

<400> SEQUENCE: 36
tcattctgaa gactagctgt ctgtga                                         26

<210> SEQ ID NO 37
<211> LENGTH: 28
<212> TYPE: DNA
<213> ORGANISM: Zea mays

<400> SEQUENCE: 37
gaaactgtga tctatggaaa gtctatgc                                       28

<210> SEQ ID NO 38
<211> LENGTH: 20
<212> TYPE: DNA
<213> ORGANISM: Zea mays

<400> SEQUENCE: 38
ccttcgcacg ggtaaactgt                                                20

<210> SEQ ID NO 39
<211> LENGTH: 23
<212> TYPE: DNA
<213> ORGANISM: Zea mays

<400> SEQUENCE: 39
gcatcatcat ccctgttgtg aag                                            23

<210> SEQ ID NO 40
<211> LENGTH: 25
<212> TYPE: DNA
<213> ORGANISM: Zea mays

<400> SEQUENCE: 40
agtacaacaa taaacagcgg agctt                                          25

<210> SEQ ID NO 41
<211> LENGTH: 21
<212> TYPE: DNA
<213> ORGANISM: Zea mays

<400> SEQUENCE: 41
tcgaggtcca acaatcacca a                                              21

<210> SEQ ID NO 42
<211> LENGTH: 20

<212> TYPE: DNA
<213> ORGANISM: Zea mays

<400> SEQUENCE: 42
catggcgata gcagtttcca                                          20

<210> SEQ ID NO 43
<211> LENGTH: 28
<212> TYPE: DNA
<213> ORGANISM: Zea mays

<400> SEQUENCE: 43
cctagctttg tttgaatgcc atactata                                 28

<210> SEQ ID NO 44
<211> LENGTH: 22
<212> TYPE: DNA
<213> ORGANISM: Zea mays

<400> SEQUENCE: 44
taaggaatga attccccagt cg                                       22

<210> SEQ ID NO 45
<211> LENGTH: 21
<212> TYPE: DNA
<213> ORGANISM: Zea mays

<400> SEQUENCE: 45
ggcactctcg cttctgttga t                                        21

<210> SEQ ID NO 46
<211> LENGTH: 25
<212> TYPE: DNA
<213> ORGANISM: Zea mays

<400> SEQUENCE: 46
ttggtgctgt ttgattgttc tacag                                    25

<210> SEQ ID NO 47
<211> LENGTH: 21
<212> TYPE: DNA
<213> ORGANISM: Zea mays

<400> SEQUENCE: 47
ccccttgtat gcatgaaatc g                                        21

<210> SEQ ID NO 48
<211> LENGTH: 21
<212> TYPE: DNA
<213> ORGANISM: Zea mays

<400> SEQUENCE: 48
accatggacg acgacatctt c                                        21

<210> SEQ ID NO 49
<211> LENGTH: 22
<212> TYPE: DNA
<213> ORGANISM: Zea mays

<400> SEQUENCE: 49
tgcagggatt ggttttttctt tt                                      22

<210> SEQ ID NO 50

-continued

```
<211> LENGTH: 23
<212> TYPE: DNA
<213> ORGANISM: Zea mays

<400> SEQUENCE: 50
ggctgattgc atatgaacat ggt                                      23

<210> SEQ ID NO 51
<211> LENGTH: 15
<212> TYPE: DNA
<213> ORGANISM: Zea mays

<400> SEQUENCE: 51
atgcatgctg ttaac                                               15

<210> SEQ ID NO 52
<211> LENGTH: 17
<212> TYPE: DNA
<213> ORGANISM: Zea mays

<400> SEQUENCE: 52
catctctgcc taccata                                             17

<210> SEQ ID NO 53
<211> LENGTH: 15
<212> TYPE: DNA
<213> ORGANISM: Zea mays

<400> SEQUENCE: 53
tcacttctca aggct                                               15

<210> SEQ ID NO 54
<211> LENGTH: 17
<212> TYPE: DNA
<213> ORGANISM: Zea mays

<400> SEQUENCE: 54
ccaatcatct aggctgc                                             17

<210> SEQ ID NO 55
<211> LENGTH: 16
<212> TYPE: DNA
<213> ORGANISM: Zea mays

<400> SEQUENCE: 55
cctgtaatcg acattt                                              16

<210> SEQ ID NO 56
<211> LENGTH: 15
<212> TYPE: DNA
<213> ORGANISM: Zea mays

<400> SEQUENCE: 56
tactggctgg aaatg                                               15

<210> SEQ ID NO 57
<211> LENGTH: 16
<212> TYPE: DNA
<213> ORGANISM: Zea mays

<400> SEQUENCE: 57
atcttcacat aactcc                                              16
```

-continued

```
<210> SEQ ID NO 58
<211> LENGTH: 14
<212> TYPE: DNA
<213> ORGANISM: Zea mays

<400> SEQUENCE: 58
acaccgaggc ttaa                                                     14

<210> SEQ ID NO 59
<211> LENGTH: 14
<212> TYPE: DNA
<213> ORGANISM: Zea mays

<400> SEQUENCE: 59
agagctgtgc ttcc                                                     14

<210> SEQ ID NO 60
<211> LENGTH: 13
<212> TYPE: DNA
<213> ORGANISM: Zea mays

<400> SEQUENCE: 60
tgtgggcttt ggc                                                      13

<210> SEQ ID NO 61
<211> LENGTH: 18
<212> TYPE: DNA
<213> ORGANISM: Zea mays

<400> SEQUENCE: 61
agatcaagta cataagca                                                 18

<210> SEQ ID NO 62
<211> LENGTH: 15
<212> TYPE: DNA
<213> ORGANISM: Zea mays

<400> SEQUENCE: 62
tctcccgtgg atgga                                                    15

<210> SEQ ID NO 63
<211> LENGTH: 17
<212> TYPE: DNA
<213> ORGANISM: Zea mays

<400> SEQUENCE: 63
tgaagatgca tcgagcc                                                  17

<210> SEQ ID NO 64
<211> LENGTH: 15
<212> TYPE: DNA
<213> ORGANISM: Zea mays

<400> SEQUENCE: 64
tgctaggaat tatgc                                                    15

<210> SEQ ID NO 65
<211> LENGTH: 14
<212> TYPE: DNA
<213> ORGANISM: Zea mays

<400> SEQUENCE: 65
cggactccat taat                                                     14
```

```
<210> SEQ ID NO 66
<211> LENGTH: 17
<212> TYPE: DNA
<213> ORGANISM: Zea mays

<400> SEQUENCE: 66
aatgcatact gttaacc                                                  17

<210> SEQ ID NO 67
<211> LENGTH: 17
<212> TYPE: DNA
<213> ORGANISM: Zea mays

<400> SEQUENCE: 67
catctctgcc tactata                                                  17

<210> SEQ ID NO 68
<211> LENGTH: 16
<212> TYPE: DNA
<213> ORGANISM: Zea mays

<400> SEQUENCE: 68
ctcacttatc aaggct                                                   16

<210> SEQ ID NO 69
<211> LENGTH: 16
<212> TYPE: DNA
<213> ORGANISM: Zea mays

<400> SEQUENCE: 69
caatcatcca ggctgc                                                   16

<210> SEQ ID NO 70
<211> LENGTH: 16
<212> TYPE: DNA
<213> ORGANISM: Zea mays

<400> SEQUENCE: 70
tgttcctgta attgac                                                   16

<210> SEQ ID NO 71
<211> LENGTH: 14
<212> TYPE: DNA
<213> ORGANISM: Zea mays

<400> SEQUENCE: 71
actgggtgga aatg                                                     14

<210> SEQ ID NO 72
<211> LENGTH: 14
<212> TYPE: DNA
<213> ORGANISM: Zea mays

<400> SEQUENCE: 72
tcttcgcata actc                                                     14

<210> SEQ ID NO 73
<211> LENGTH: 14
<212> TYPE: DNA
<213> ORGANISM: Zea mays

<400> SEQUENCE: 73
acaccgagcc ttaa                                                     14
```

```
<210> SEQ ID NO 74
<211> LENGTH: 14
<212> TYPE: DNA
<213> ORGANISM: Zea mays

<400> SEQUENCE: 74
agagcagtgc ttcc                                                     14

<210> SEQ ID NO 75
<211> LENGTH: 16
<212> TYPE: DNA
<213> ORGANISM: Zea mays

<400> SEQUENCE: 75
tgtgggtttt ggcact                                                   16

<210> SEQ ID NO 76
<211> LENGTH: 15
<212> TYPE: DNA
<213> ORGANISM: Zea mays

<400> SEQUENCE: 76
tcaagtgcat aagca                                                    15

<210> SEQ ID NO 77
<211> LENGTH: 16
<212> TYPE: DNA
<213> ORGANISM: Zea mays

<400> SEQUENCE: 77
ttctcctgtg gatgga                                                   16

<210> SEQ ID NO 78
<211> LENGTH: 15
<212> TYPE: DNA
<213> ORGANISM: Zea mays

<400> SEQUENCE: 78
aagatgcgtc gagcc                                                    15

<210> SEQ ID NO 79
<211> LENGTH: 15
<212> TYPE: DNA
<213> ORGANISM: Zea mays

<400> SEQUENCE: 79
tgctaggaat aatgc                                                    15

<210> SEQ ID NO 80
<211> LENGTH: 14
<212> TYPE: DNA
<213> ORGANISM: Zea mays

<400> SEQUENCE: 80
ccggacacca ttaa                                                     14
```

US 11,032,986 B2

METHODS OF CREATING DROUGHT TOLERANT CORN PLANTS USING MARKERS LINKED TO COLD SHOCK DOMAIN-CONTAINING PROTEINS AND COMPOSITIONS THEREOF

CROSS-REFERENCE TO RELATED APPLICATIONS

This application is a divisional of U.S. application Ser. No. 14/072,081, filed Nov. 5, 2013, which application claims the benefit under 35 U.S.C. § 119(e) U. S. Provisional Application No. 61/723,378, filed 7 Nov. 2012. The entirety of each of the foregoing applications is hereby incorporated by reference.

INCORPORATION OF SEQUENCE LISTING

A sequence listing containing the file named "57823_SeqList.txt" which is 48,512 bytes (measured in MS-Windows®) and created on 26 Sep. 2012 comprises 80 nucleotide sequences, and is herein incorporated by reference in its entirety

FIELD OF THE INVENTION

The invention relates to methods and compositions used to improve the tolerance of corn to drought, or low water conditions, or otherwise improving water use efficiency (WUE). Embodiments of the invention include methods of detecting drought tolerance alleles and providing drought tolerance in elite germplasm containing one or more drought tolerance loci. Also disclosed are transgenic plants comprising recombinant DNA providing drought tolerance, including cells, seed, and pollen derived from such a plant, as well as methods of making and using such plants.

SUMMARY

This section provides a general summary of the disclosure, and is not a comprehensive disclosure of its full scope or all of its features.

Identifying and selecting plants that exhibit tolerance to dry conditions using marker-assisted selection (MAS) provides an effective and efficient method of improving the survivability of crops during times of drought. For a genetic marker to be effective in MAS for a drought tolerance trait, its inheritance must be accurately associated or correlated with the inheritance of drought tolerance. Generating accurate drought tolerance markers, however, is especially difficult due to the complexity of growing plants in controlled trials on a large scale where the inheritance of drought tolerance can be reliably scored. What is needed are more direct methods of finding genes or genetic loci that affect drought tolerance as well as genetically linked markers that cosegregate with them so that the genes or loci can be reliably detected and tracked during MAS to create populations with enhanced drought tolerance.

The present invention includes a method that employs nucleic acid sequences associated with cold-shock domains (CSDs) to identify DNA sequences and chromosome intervals in a plant genome that are associated with drought tolerance. Two such cold-shock associated sequences identified using this method, csd1 and csd2, correspond to genes in the corn genome on chromosome 4 and chromosome 10, respectively. Chromosome intervals linked to csd1 and csd2 that were subsequently characterized and associated with drought tolerance are also described herein. This method can be used to detect other drought tolerance loci and flanking chromosome intervals in any species of plant through the identification of analogous or homologous cold-shock domains.

A number of suitable corn marker loci and quantitative trait loci (QTL) chromosome intervals that demonstrate statistically significant cosegregation with drought tolerance are provided. These markers, or additional loci linked to these markers, can be used in MAS breeding programs to produce plants with improved drought tolerance.

Embodiments of this invention also include identifying one or more corn plants with drought tolerance, improved tolerance, or susceptibility to drought by using a marker within the CSD1 chromosome interval, or a marker closely linked to csd1. Other embodiments of this invention also include identifying one or more corn plants with drought tolerance, improved tolerance, or susceptibility to drought by using a marker within the CSD2 chromosome interval, or a marker closely linked to csd2. As used herein, "closely linked" means that the marker or locus is within about 20 cM, preferably within about 15 cM, more preferably within about 10 cM, even more preferably within about 5 cM, even more preferably within about 1 cM, even more preferably about 0.5 cM, and even more preferably less than 0.5 cM of the identified cold-shock gene or domain.

Locations in the maize genome of csd1 and csd2, and the chromosome intervals genetically linked to them, are referenced herein to the public maize genome map IBM2 Neighbors 2008 and illustrated in Table 1. Genomic markers such as IDP7557 and isu61b can be used to define the flanks of a chromosome interval containing csd1. The genomic markers bnlg1028 and rz569a can be used to define the flanks of a chromosome interval containing csd2. Other genomic markers may be used to define chromosome sub-intervals linked to csd1 or csd2.

In one embodiment, a population of corn plants with enhanced drought tolerance is created by detecting the presence of genetic markers that are associated with a drought tolerance trait (a drought tolerance phenotype) and that are genetically linked to and within 20 cM of the csd1 gene of at least one corn plant in a first population. Then, the one or more corn plants that exhibit the drought tolerance genotype is selected from the first population and used to produce an offspring population that exhibits enhanced drought tolerance as compared to the first population. In other embodiments, the drought tolerance genotypes used are within 10 cM, 5 cM, 1 cM, or 0.5 cM of the csd1 gene.

Embodiments of this invention also include creating a population of corn plants with enhanced drought tolerance by detecting the presence of genetic markers that are associated with a drought tolerance trait (a drought tolerance phenotype) and that are within the CSD1 chromosome interval of at least one corn plant in a first population. Then, the one or more corn plants that exhibit the drought tolerance genotype is selected from the first population and used to produce an offspring population that exhibits enhanced drought tolerance as compared to the first population. The CSD1 chromosome interval includes the csd1 sequence (SEQ ID NO. 1) and includes any marker within the region flanked by IDP7557 and isu61b, including IDP7557 and isu61b. Sub-intervals of CSD1 are also useful, and include any interval wherein one or both borders of the sub-interval are between IDP7557 and isu61b, including IDP7557 or isu61b. In one embodiment, a CSD1 sub-interval is flanked by, and includes, SEQ ID NO. 5 and SEQ ID NO. 12. In another embodiment, a CSD1 sub-interval is flanked by, and includes, dp1 and TIDP5664. In another embodiment, a CSD1 sub-interval is flanked by, and includes, umc109 and gpm167a. All manner of chromosome interval lengths between, and including, IDP7551 and isu61b can be used in conjunction with this invention. This invention also includes any corn plant created by these methods.

In one embodiment, a population of corn plants with enhanced drought tolerance is created by detecting the presence of genetic markers that are associated with a drought tolerance trait (a drought tolerance phenotype) and that are genetically linked to and within 20 cM of the csd2 gene of at least one corn plant in a first population. Then, the one or more corn plants that exhibit the drought tolerance genotype is selected from the first population and used to produce an offspring population that exhibits enhanced drought tolerance as compared to the first population. In other embodiments, the drought tolerance genotypes used are within 10 cM, 5 cM, 1 cM, or 0.5 cM of the csd2 gene.

Embodiments of this invention also include creating a population of corn plants with enhanced drought tolerance by detecting the presence of genetic markers that are associated with a drought tolerance trait (a drought tolerance phenotype) and that are within the CSD2 chromosome interval of at least one corn plant in a first population. Then, the one or more corn plants that exhibit the drought tolerance genotype is selected from the first population and used to produce an offspring population that exhibits enhanced drought tolerance as compared to the first population. The CSD2 chromosome interval includes the csd2 sequence (SEQ ID NO. 2) and includes any marker flanked by bnlg1028 and rz569a. Sub-intervals of CSD1 are also useful, and include any interval wherein one or both borders of the sub-interval are between bnlg1028 and rz569a, including bnlg1028 or rz569a. In one embodiment, a CSD2 sub-interval is flanked by, and includes, TIDP3345 and SEQ ID NO. 19. In another embodiment, a CSD2 sub-interval is flanked by, and includes, IDP4016 and IDP7187. In another embodiment, a CSD2 sub-interval is flanked by, and includes, IDP8964 and gpm691a. All manner of chromosome interval lengths between, and including, bnlg1028 and rz569a can be used in conjunction with this invention. This invention also includes any corn plant created by these methods.

In other embodiments, the frequency of a drought tolerance phenotype in a population of corn plants is increased by detecting the presence of genetic markers that are associated with a drought tolerance trait (a drought tolerance phenotype) and that are genetically linked to and within 20 cM of csd1 in a first population of corn plants. Then, one or more corn plants exhibiting the drought tolerance genotype from the first population are selected and used to produce an offspring population wherein the drought tolerance phenotype occurs more frequently in the offspring population as compared to the first population. In other embodiments, the drought tolerance genotypes used are within 10 cM, 5 cM, 1 cM, or 0.5 cM of the csd1 gene.

Embodiments of this invention also include increasing the frequency of a drought tolerance phenotype in a population of corn plants by detecting the presence of genetic markers that are associated with a drought tolerance trait (a drought tolerance phenotype) and that are within the CSD1 chromosome interval, which includes the csd1 sequence (SEQ ID NO. 1) or any marker within the chromosome interval flanked by IDP7557 and isu61b, including IDP7557 and isu61b. Sub-intervals of CSD1 are also useful for increasing the frequency of a drought tolerance phenotype in a population of corn plants, and embodiments of this invention include using any marker on a chromosome interval wherein one or both borders of the sub-interval are between IDP7557 and isu61b, including IDP7557 or isu61b. In one embodiment, a CSD1 sub-interval is flanked by, and includes, SEQ ID NO. 5 and SEQ ID NO. 12. In another embodiment, a CSD1 sub-interval is flanked by, and includes, dp1 and TIDP5664. In another embodiment, a CSD1 sub-interval is flanked by, and includes, umc109 and gpm167a. All manner of chromosome interval lengths between, and including, IDP7551 and isu61b can be used in conjunction with this invention. This invention also includes any corn plant created by these methods.

In yet another embodiment, the frequency of a drought tolerance phenotype in a population of corn plants is increased by detecting the presence of genetic markers that are associated with a drought tolerance trait (a drought tolerance phenotype) and that are genetically linked to and within 20 cM of csd2 in a first population of corn plants. Then, one or more corn plants exhibiting the drought tolerance genotype from the first population are selected and used to produce an offspring population wherein the drought tolerance phenotype occurs more frequently in the offspring population as compared to the first population. In other embodiments, the drought tolerance genotypes used are within 10 cM, 5 cM, 1 cM, or 0.5 cM of the csd2 gene.

Embodiments of this invention also include increasing the frequency of a drought tolerance phenotype in a population of corn plants by detecting the presence of genetic markers that are associated with a drought tolerance trait (a drought tolerance phenotype) and that are within the CSD2 chromosome interval, which includes the csd2 sequence (SEQ ID NO. 2) or any marker flanked by bnlg1028 and rz569a. Sub-intervals of CSD2 are also useful for increasing the frequency of drought tolerance phenotypes in a population, and include any interval wherein one or both borders of the sub-interval are between bnlg1028 and rz569a, including bnlg1028 or rz569a. In one embodiment, a CSD2 sub-interval is flanked by, and includes, TIDP3345 and SEQ ID NO. 19. In another embodiment, a CSD2 sub-interval is flanked by, and includes, IDP4016 and IDP7187. In another embodiment, a CSD2 sub-interval is flanked by, and includes, IDP8964 and gpm691a. All manner of chromosome interval lengths between, and including, bnlg1028 and rz569a can be used in conjunction with this invention. This invention also includes any corn plant created by these methods.

Another embodiment of this invention includes a plant cell containing a recombinant DNA construct comprising a first nucleic acid sequence exhibiting greater than 80% homology with a either csd1 or csd2, wherein said recombinant DNA construct confers enhanced drought tolerance. Transgenic expression of drought tolerance alleles may involve the construction of appropriate DNA transformation and expression vectors, and may also employ specialized promoters and other expression elements operably linked to one or more drought tolerance alleles, which are features of this invention. These embodiments can be used with any species of plant.

This invention also includes methods of identifying the drought tolerance potential of a plant by analyzing one or more endogenous nucleotide sequences of a plant to detect the presence of genetic markers closely linked to a cold-shock domain and then testing the plant's performance under drought conditions. In some embodiments, the plant

DETAILED DESCRIPTION

CSDs as Drought Tolerance Loci

It has been discovered that endogenous cold-shock-related sequences in a plant genome can affect drought tolerance of the plant. Plant breeders skilled in the art can now use this information to more efficiently identify plants containing nucleic acid sequences that affect drought tolerance, including new drought tolerance genes or loci. Once identified, genetic markers associated with the drought tolerance genes or loci can be identified and used to select one or more plants exhibiting drought tolerance via MAS, thus producing populations of plants with improved drought tolerance.

In one embodiment, a DNA sequence associated with cold-shock response in a bacterium can be used in conjunction with a BLAST® (basic local alignment search tool) search to target similar sequences in a plant genome. It is anticipated that one skilled in the art can then further test the targeted sequences to characterize their drought tolerance properties using methods described herein, or others that are described in the art. In other embodiments, protein sequences known for their cold-shock properties in one plant species can be used to BLAST® (basic local alignment search tool) for similar sequences in another plant species with further evaluation of the drought tolerance properties of the targeted sequences to follow.

This method greatly facilitates the identification of potential drought tolerance sequences in a plant genome, bypassing the difficult and confounding process of identifying drought tolerance sequences by previous methods known in the art.

Chromosome Intervals

The term "chromosome interval" designates a contiguous linear span of genomic DNA that resides in planta on a single chromosome. The term also designates any and all genomic intervals defined by any of the markers set forth in this invention. The genetic elements located on a single chromosome interval are physically linked and the size of a chromosome interval is not particularly limited. In some aspects, the genetic elements located within a single chromosome interval are genetically linked, typically with a genetic recombination distance of, for example, less than or equal to 20 cM, or alternatively, less than or equal to 10 cM. That is, two genetic elements within a single chromosome interval undergo recombination at a frequency of less than or equal to 20% or 10%, respectively.

The boundaries of chromosome intervals comprise markers that will be linked to the gene, genes, or loci providing the trait of interest, i.e. any marker that lies within a given interval, including the terminal markers that define the boundaries of the interval, can be used as a marker for drought tolerance. The intervals described herein encompass marker clusters that co-segregate with drought tolerance. The clustering of markers occurs in relatively small domains on the chromosomes, indicating the presence of a genetic locus controlling the trait of interest in those chromosome regions. The interval encompasses markers that map within the interval as well as the markers that define the terminal.

An interval described by the terminal markers that define the endpoints of the interval will include the terminal markers and any marker localizing within that chromosome domain, whether those markers are currently known or unknown. Although it is anticipated that one skilled in the art may describe additional polymorphic sites at marker loci in and around the markers identified herein, any marker within the chromosome intervals described herein that are associated with drought tolerance fall within the scope of this claimed invention.

"Quantitative trait loci" or a "quantitative trait locus" (QTL) is a genetic domain that effects a phenotype that can be described in quantitative terms and can be assigned a "phenotypic value" which corresponds to a quantitative value for the phenotypic trait. A QTL can act through a single gene mechanism or by a polygenic mechanism. The boundaries of chromosome intervals are drawn to encompass markers that will be linked to one or more QTL. In other words, the chromosome interval is drawn such that any marker that lies within that interval (including the terminal markers that define the boundaries of the interval) can be used as markers for drought tolerance. Each interval comprises at least one QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identifying the same QTL or two different QTL. Regardless, knowledge of how many QTL are in a particular interval is not necessary to make or practice the invention.

The Chromosome Intervals of this Invention

In one embodiment, the present invention provides a plant comprising a nucleic acid molecule selected from the group consisting of SEQ ID NO: 1-20 or fragments thereof, and complements of both. The present invention also provides a plant comprising alleles of csd1 or csd2 or fragments and complements thereof as well as any plant comprising any combination of one or more drought tolerance loci selected from the group consisting of SEQ ID NOs: 1-20. Such alleles may be homozygous or heterozygous.

The location in the maize genome of csd1 and the chromosome interval CSD1 comprising markers closely linked to csd1 are disclosed in Table 1a. The location in the maize genome of csd2 and the CSD2 chromosome interval comprising markers closely linked to csd2 are disclosed in Table 1b. Genetic map loci are represented in cM, with position zero being the first (most distal) marker known at the beginning of the chromosome on both Monsanto's internal consensus genetic map and the Neighbors 2008 maize genomic map, which is freely available to the public from the Maize GDB website and commonly used by those skilled in the art. Also disclosed in Tables 1a and 1b are the physical locations of loci as they are reported on the B73 RefGen_v2 sequence public assembly by the Arizona Genomics Institute.

TABLE 1a

Genetic and physical map positions of markers associated with the csd1 gene and the CSD1 chromosome interval.

| Marker/ Locus | Relative Genetic Map Position† | | Physical Map Position†† | | |
|---|---|---|---|---|---|
| | MON Map (cM) | IBM2 Map (IcM) | Contig | Chr Start | Chr End |
| IDP7557 | 182.2 | 637.7 | AC183908.3 | 234,900,889 | 234,902,655 |
| npi294g | 182.5 | 639.2 | * | * | * |
| cl14668_1 | 182.6 | 639.3 | * | * | * |

TABLE 1a-continued

Genetic and physical map positions of markers associated with the csd1 gene and the CSD1 chromosome interval.

| Marker/Locus | Relative Genetic Map Position† | | Physical Map Position†† | | |
|---|---|---|---|---|---|
| | MON Map (cM) | IBM2 Map (IcM) | Contig | Chr Start | Chr End |
| gpm516 | 183.4 | 642.8 | * | * | * |
| IDP7037 | 183.4 | 642.8 | AC196075.2 | 235208769 | 235209884 |
| SEQ ID NO. 3 | 183.4 | 647.2 | * | * | * |
| SEQ ID NO. 4 | 190.6 | 666.7 | * | * | * |
| umc1532 | 192.6 | 671.9 | AC191145.3 | 236,951,290 | 236,951,758 |
| umc124b (chk) | 192.9 | 672.4 | * | * | * |
| SEQ ID NO. 5 | 193 | 672.5 | * | * | * |
| gpm803b | 194.6 | 675 | * | * | * |
| IDP7964 | 195 | 675.7 | AC196269.3 | 237,268,329 | 237,270,871 |
| SEQ ID NO. 6 | 195.3 | 676.1 | * | * | * |
| SEQ ID NO. 7 | 195.6 | 676.5 | * | * | * |
| SEQ ID NO. 8 | 195.6 | 676.5 | * | * | * |
| dp1 | 198.5 | 680.9 | * | * | * |
| TIDP6218 | 201.3 | 685.3 | AC205324.3 | 237,885,508 | 237,887,188 |
| umc1109 | 202.9 | 687.8 | AC204715.3 | 238,121,854 | 238,122,563 |
| csd1 (SEQ ID NO. 1) | 203.3 | 688.7 | * | * | * |
| lim471a | 203.3 | 688.7 | AC204715.3 | 238,121,854 | 238,286,403 |
| gpm167a | 204.4 | 691.11 | * | * | * |
| umc2288 | 204.8 | 692.1 | AC204715.3 | 238,285,686 | 238,286,403 |
| SEQ ID NO. 9 | 205.1 | 693 | * | * | * |
| TIDP5664 | 208.6 | 702.91 | AC191360.3 | 238,431,333 | 238,433,416 |
| SEQ ID NO. 10 | 209.3 | * | * | * | * |
| SEQ ID NO. 11 | 210.3 | 210.3 | * | * | * |
| IDP3969 | 212.9 | 715.3 | AC205853.3 | 239206097 | 239209568 |
| AY109611 | 213 | 715.5 | * | * | * |
| SEQ ID NO. 12 | 213.4 | 729.8 | * | * | * |
| cpn10 | 213.5 | 716.9 | * | * | * |
| IDP6899 | 214.1 | 718.8 | AC208362.3 | 239,412,399 | 239,415,497 |
| mmp182 | 221.7 | 740.7 | AC183888.4 | 240,236,279 | 240,236,805 |
| isu61b | 223.4 | 745.6 | * | * | * |

†cM = centiMorgans, IcM = map units of the IBM2 2008 Neighbors Genetic Map.
††Arizona Genomics Institute B73 RefGen_v2 sequence.
* Exact coordinates not known. Coordinates can be estimated based on nearest flanking loci with known coordinates.

TABLE 1b

Genetic and physical map positions of markers associated with the csd2 gene and the CSD2 chromosome interval.

| Marker/Locus | Relative Genetic Map Position† | | Physical Map Position†† | | |
|---|---|---|---|---|---|
| | MON Map (cM) | IBM2 Map (IcM) | Contig | Chr Start | Chr End |
| bnlg1028 | 83.9 | 380.5 | AF66202.2 | 138,475,535 | 138,476,414 |
| gar2 | 84 | 381 | * | * | * |
| SEQ ID NO. 13 | 84.1 | 381.3 | * | * | * |
| IDP7210 | 84.2 | 381.8 | AC199387 | 138298559 | 138300324 |
| IDP134 | 85 | 385 | AC231226.2 | 138858044 | 138860737 |
| IDP7440 | 85.3 | 386.4 | AC199392.4 | 139010553 | 139012360 |
| SEQ ID NO. 14 | 91.9 | 407.3 | * | * | * |
| TIDP3345 | 95 | 415.8 | AC204716.3 | 142186249 | 142189921 |
| pza02519 | 95.3 | 416.5 | * | * | * |
| ufg62 | 95.3 | 416.6 | * | * | * |
| IDP3850 | 95.8 | 418.17 | AC191543.3 | 142,333,967 | 142,336,197 |
| SEQ ID NO. 15 | 97.5 | 424 | * | * | * |
| IDP4016 | 99.5 | 430.76 | AC183945.3 | 143,065,469 | 143,069,365 |
| IDP8964 | 104.6 | 448.05 | AC195335.3 | 146,170,179 | 146,173,470 |
| npi321a | 105.1 | 449.3 | * | * | * |
| csd2 (SEQ ID NO. 2) | 105.2 | 450 | | | |
| sgb103 | 105.3 | 450 | * | * | * |
| AY110016 | 105.4 | 450.8 | AC197497.3 | 144,469,525 | 144,470,299 |
| SEQ ID NO. 16 | 106 | * | * | * | * |
| gpm691a | 106.1 | 453.5 | * | * | * |
| IDP8439 | 110.1 | 463.7 | AC200322.4 | 147,896,477 | 147,898,461 |
| IDP7187 | 110.5 | 464.8 | AC200742.3 | 148,105,248 | 148,106,642 |
| SEQ ID NO. 17 | 113 | 113 | * | * | * |
| SEQ ID NO. 18 | 114 | 114 | * | * | * |
| TIDP3378 | 114.3 | 473.4 | AC214046.4 | 148,996,063 | 148,998,265 |
| pco137999 | 114.4 | 473.4 | * | * | * |
| SEQ ID NO. 19 | 116.3 | 478 | * | * | * |
| csu300b | 117 | 479.9 | * | * | * |
| SEQ ID NO. 20 | 118.3 | 118.3 | * | * | * |
| bnlg1450 | 118.6 | 483.7 | AC190651.2 | 146,358,351 | 146,359,143 |
| php20568a | 122.7 | 496.6 | * | * | * |
| rz569a | 126.2 | 502.9 | * | * | * |

†cM = centiMorgans, IcM = map units of the IBM2 2008 Neighbors Genetic Map.
††Arizona Genomics Institute B73 RefGen_v2 sequence.
* Exact coordinates not known. Coordinates can be estimated based on nearest flanking loci with known coordinates.

In Table 1, "IcM" refers to the map units of the IBM2 2008 Neighbors Genetic Map, which was generated with an intermated recombinant inbred population (syn 4) that resulted in approximately a four-fold increase in the number of meioses as compared to the typical recombination experiment that is used to generate centiMorgan (cM) distances (Lee et al., 2002, Plant Mol Biol 48:453 and the Maize Genetics and Genomics Database). "cM" refers to the classical definition of a centimorgan (Haldane 1919 J Genet 8:299-309) wherein one cM is equal to a 1% chance that a trait at one genetic locus will be separated from a trait at another locus due to crossing over in a single meiosis (meaning the traits cosegregate 99% of the time), and this definition is used herein to delineate map locations pertaining to this invention.

For example, the CSD1 chromosome interval contains csd1 (SEQ ID NO. 1) and is flanked by the markers IDP7557 and isu61b, which are separated by approximately 41 cM on the internally-derived genetic map. This chromosome interval encompasses a marker cluster that co-segregates with drought tolerance in the populations studied at a p-value ≤0.05. An example of a subinterval of the CSD1 interval includes TIDP6218 and gpm167a, separated by approximately 3 cM on the internally-derived genetic map, that define a chromosome interval encompassing a cluster of markers that co-segregate with drought tolerance in the populations studied at a p-level ≤0.05.

Likewise, the CSD2 chromosome interval contains csd2 (SEQ ID NO. 2), and includes the flanking markers bnlg1028 and rz569a, separated by approximately 42 cM on the internally-derived genetic map, which define a chromosome interval encompassing a marker cluster that co-segregates with drought tolerance in the populations studied at a p-value ≤0.05. An example of a subinterval of the CSD2 interval includes npi321a and AY110016, separated by approximately 0.3 cM, that define a chromosome interval encompassing a cluster of markers that co-segregate with drought tolerance in the populations studied at a p-level ≤0.05. Features of this invention include any subinterval based on markers within the CSD1 or CSD2 chromosome intervals, including any markers within the csd1 or csd2 genes and/or any markers closely linked to the csd1 or csd2 genes.

Thus, one skilled in the art can use this invention to improve the efficiency of breeding for improved drought tolerance in maize by associating drought tolerance phenotypes with genotypes linked to the csd1 or csd2 genes. Disclosed herein are chromosome intervals that comprise alleles responsible for phenotypic differences between drought tolerant and drought susceptible corn lines. Each chromosome interval is characterized by the genomic regions including and flanking the endogenous csd1 or csd2 genes and comprise markers within or closely linked to csd1 or csd2.

The CSD1 chromosome interval includes the csd1 sequence (SEQ ID NO. 1) and any marker within the interval flanked by IDP7557 and isu61b, including IDP7557 and isu61b. Sub-intervals of CSD1 are also useful, and include any interval whose borders are between IDP7557 and isu61b, including IDP7557 or isu61b.

The CSD2 chromosome interval includes the csd2 sequence (SEQ ID NO. 2) and includes any marker within the interval flanked by bnlg1028 and rz569a, including bnlg1028 and rz569a. Sub-intervals of CSD2 are also useful, and include any interval whose borders are between bnlg1028 and rz569a, including bnlg1028 and rz569a.

Embodiments of this invention include identifying one or more corn plants with drought tolerance, improved tolerance, or susceptibility to drought by using a marker within the CSD1 or CSD2 chromosome interval, or a marker closely linked to csd1 or csd2.

Accordingly, the markers and methods of the present invention can be utilized to guide MAS or breeding maize varieties with the desired complement (set) of allelic forms of chromosome intervals associated with superior agronomic performance (tolerance, along with any other available markers for yield, tolerance to disease or environmental conditions, etc.). Any of the disclosed marker alleles can be introduced into a corn line via introgression, by traditional breeding (or introduced via transformation, or both) to yield a corn plant with superior agronomic performance. The number of alleles associated with tolerance that can be introduced or be present in a corn plant of the present invention ranges from 1 to the number of alleles disclosed herein, each integer of which is incorporated herein as if explicitly recited.

MAS using additional markers flanking either side of the DNA locus provide further efficiency because an unlikely double recombination event would be needed to simultaneously break linkage between the locus and both markers.

Moreover, using markers tightly flanking a locus, one skilled in the art of MAS can reduce linkage drag by more accurately selecting individuals that have less of the potentially deleterious donor parent DNA. Any marker linked to or among the chromosome intervals described herein could be useful and within the scope of this invention.

Similarly, by identifying plants lacking the desired marker locus, susceptible or less tolerant plants can be identified, and, e.g., eliminated from subsequent crosses. Similarly, these marker loci can be introgressed into any desired genomic background, germplasm, plant, line, variety, etc., as part of overall MAS breeding program designed to enhance drought tolerance and/or yield. The invention also provides chromosome QTL intervals that find equal use in MAS to select plants that demonstrate drought tolerance or improved tolerance. Similarly, the QTL intervals can also be used to counter-select plants that are susceptible or have reduced tolerance to low water conditions.

The present invention also extends to a method of making a progeny corn plant and these progeny corn plants, per se. The method comprises crossing a first parent corn plant with a second corn plant and growing the female corn plant under plant growth conditions to yield corn plant progeny. Methods of crossing and growing corn plants are well within the ability of those of ordinary skill in the art. Such corn plant progeny can be assayed for alleles associated with tolerance and, thereby, the desired progeny selected. Such progeny plants or seed can be sold commercially for corn production, used for food, processed to obtain a desired constituent of the corn, or further utilized in subsequent rounds of breeding. At least one of the first or second corn plants is a corn plant of the present invention in that it comprises at least one of the allelic forms of the markers of the present invention, such that the progeny are capable of inheriting the allele.

Often, a method of the present invention is applied to at least one related corn plant such as from progenitor or descendant lines in the subject corn plants' pedigree such that inheritance of the desired tolerance allele can be traced. The number of generations separating the corn plants being subject to the methods of the present invention will generally be from 1 to 20, commonly 1 to 5, and typically 1, 2, or 3 generations of separation, and quite often a direct descendant or parent of the corn plant will be subject to the method (i.e., one generation of separation).

Thus, with this invention, one skilled in the art can detect the presence or absence of drought tolerance genotypes in the genomes of corn plants as part of a marker assisted selection program. In one embodiment, a breeder ascertains the genotype at one or more markers for a drought tolerant parent, which contains a drought tolerance allele, and the genotype at one or more markers for a susceptible parent, which lacks the tolerance allele. For example, the markers of the present invention can be used in MAS in crosses involving elite×exotic corn lines by subjecting the segregating progeny to MAS to maintain drought tolerance alleles, or alleles associated with yield under low water conditions. A breeder can then reliably track the inheritance of the tolerance alleles through subsequent populations derived from crosses between the two parents by genotyping offspring with the markers used on the parents and comparing the genotypes at those markers with those of the parents. Depending on how tightly linked the marker alleles are with the trait, progeny that share genotypes with the drought tolerant parent can be reliably predicted to express the tolerant phenotype; progeny that share genotypes with the drought susceptible parent can be reliably predicted to express the susceptible phenotype. Thus, the laborious and inefficient process of manually phenotyping the progeny for drought tolerance is avoided.

By providing the positions in the maize genome of the intervals and the drought tolerance associated markers within, this invention also allows one skilled in the art to identify other markers linked to those disclosed herein, or linked to the chromosome intervals disclosed herein, or linked to the csd1 or csd2 loci, or within the csd1 or csd2 genes themselves, that can be used for MAS of drought tolerance.

Closely linked markers flanking the locus of interest that have alleles in linkage disequilibrium with a tolerance allele at that locus may be effectively used to select for progeny plants with enhanced tolerance to drought conditions. Thus, the markers described herein, such as those listed in Table 1, as well as other markers genetically or physically mapped to the same chromosome interval, may be used to select for maize plants with enhanced tolerance to drought conditions. Typically, a set of these markers will be used, (e.g., 2 or more, 3 or more, 4 or more, 5 or more) in the flanking region above the gene and a similar set in the flanking region below the gene. Optionally, as described above, a marker within the actual gene and/or locus may also be used. The parents and their progeny are screened for these sets of markers, and the markers that are polymorphic between the two parents are used for selection. In an introgression program, this allows for selection of the gene or locus genotype at the more proximal polymorphic markers and selection for the recurrent parent genotype at the more distal polymorphic markers.

The choice of markers actually used to practice this invention is not particularly limited and can be any marker that maps within the csd1 or csd2 sequences described herein, any marker closely linked (within about 20 cM) to a marker in the csd1 or csd2 chromosome intervals, or any marker selected from SEQ ID NOs: 1-20 or the markers listed in Table 1. Furthermore, since there are many different types of marker detection assays known in the art, it is not intended that the type of marker detection assay used to practice this invention be limited in any way.

Molecular Genetic Markers

"Marker," "genetic marker," "molecular marker," "marker nucleic acid," and "marker locus" refer to a nucleotide sequence or encoded product thereof (e.g., a protein) used as a point of reference when identifying a linked locus. A marker can be derived from genomic nucleotide sequence or from expressed nucleotide sequences (e.g., from a spliced RNA, a cDNA, etc.), or from an encoded polypeptide, and can be represented by one or more particular variant sequences, or by a consensus sequence. In another sense, a marker is an isolated variant or consensus of such a sequence. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. A "marker locus" is a locus that can be used to track the presence of a second linked locus, e.g., a linked locus that encodes or contributes to expression of a phenotypic trait. For example, a marker locus can be used to monitor segregation of alleles at a locus, such as a QTL, that are genetically or physically linked to the marker locus. Thus, a "marker allele," alternatively an "allele of a marker locus" is one of a plurality of polymorphic nucleotide sequences found at a marker locus in a population that is polymorphic for the marker locus.

"Marker" also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also know for the detection of expressed sequence tags (ESTs) and SSR markers derived from EST sequences and randomly amplified polymorphic DNA (RAPD).

A favorable allele of a marker is the allele of the marker that cosegregates with a desired phenotype (e.g., drought tolerance). As used herein, a QTL marker has a minimum of one favorable allele, although it is possible that the marker might have two or more favorable alleles found in the population. Any favorable allele of that marker can be used advantageously for the identification and construction of tolerant plant lines. Optionally, one, two, three or more favorable allele(s) of different markers are identified in, or introgressed into a plant, and can be selected for or against during MAS. Desirably, plants or germplasm are identified that have at least one such favorable allele that positively correlates with drought tolerance or improved drought tolerance. Alternatively, a marker allele that co-segregates with drought susceptibility also finds use with the invention, since that allele can be used to identify and counter select drought susceptible plants. Such an allele can be used for exclusionary purposes during breeding to identify alleles that negatively correlate with drought tolerance, to eliminate susceptible plants or germplasm from subsequent rounds of breeding.

The more tightly linked a marker is with a DNA locus influencing a phenotype, the more reliable the marker is in MAS, as the likelihood of a recombination event unlinking the marker and the locus decreases. Markers containing the causal mutation for a trait, or that are within the coding sequence of a causative gene, are ideal as no recombination is expected between them and the sequence of DNA responsible for the phenotype.

Genetic markers are distinguishable from each other (as well as from the plurality of alleles of any one particular marker) on the basis of polynucleotide length and/or sequence. A large number of corn molecular markers are known in the art, and are published or available from various sources, such as the MaizeGDB internet resource. In general, any differentially inherited polymorphic trait (including a nucleic acid polymorphism) that segregates among progeny is a potential genetic marker.

In some embodiments of the invention, one or more marker alleles are selected for in a single plant or a population of plants. In these methods, plants are selected that contain favorable alleles from more than one tolerance marker, or alternatively, favorable alleles from more than one tolerance marker are introgressed into a desired germplasm. One of skill recognizes that the identification of favorable marker alleles is germplasm-specific. The determination of which marker alleles correlate with tolerance (or susceptibility) is determined for the particular germplasm under study. One of skill recognizes that methods for identifying the favorable alleles are routine and well known in the art, and furthermore, that the identification and use of such favorable alleles is well within the scope of this invention. Furthermore still, identification of favorable marker alleles in plant populations other than the populations used or described herein is well within the scope of this invention.

Marker Detection

In some aspects, methods of the invention utilize an amplification step to detect/genotype a marker locus, but amplification is not always a requirement for marker detection (e.g. Southern blotting and RFLP detection). Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

"Amplifying," in the context of nucleic acid amplification, is any process whereby additional copies of a selected nucleic acid (or a transcribed form thereof) are produced. In some embodiments, an amplification based marker technology is used wherein a primer or amplification primer pair is admixed with genomic nucleic acid isolated from the first plant or germplasm, and wherein the primer or primer pair is complementary or partially complementary to at least a portion of the marker locus, and is capable of initiating DNA polymerization by a DNA polymerase using the plant genomic nucleic acid as a template. The primer or primer pair is extended in a DNA polymerization reaction having a DNA polymerase and a template genomic nucleic acid to generate at least one amplicon. In other embodiments, plant RNA is the template for the amplification reaction. In some embodiments, the QTL marker is a SNP type marker, and the detected allele is a SNP allele, and the method of detection is allele specific hybridization (ASH).

In general, the majority of genetic markers rely on one or more property of nucleic acids for their detection. Typical amplification methods include various polymerase based replication methods, including the polymerase chain reaction (PCR), ligase mediated methods such as the ligase chain reaction (LCR) and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like). A "genomic nucleic acid" is a nucleic acid that corresponds in sequence to a heritable nucleic acid in a cell. Common examples include nuclear genomic DNA and amplicons thereof. A genomic nucleic acid is, in some cases, different from a spliced RNA, or a corresponding cDNA, in that the spliced RNA or cDNA is processed, e.g., by the splicing machinery, to remove introns. Genomic nucleic acids optionally comprise non-transcribed (e.g., chromosome structural sequences, promoter regions, enhancer regions, etc.) and/or non-translated sequences (e.g., introns), whereas spliced RNA/cDNA typically do not have non-transcribed sequences or introns. A "template nucleic acid" is a nucleic acid that serves as a template in an amplification reaction (e.g., a polymerase based amplification reaction such as PCR, a ligase mediated amplification reaction such as LCR, a transcription reaction, or the like). A template nucleic acid can be genomic in origin, or alternatively, can be derived from expressed sequences, e.g., a cDNA or an EST. Details regarding the use of these and other amplification methods can be found in any of a variety of standard texts. Many available biology texts also have extended discussions regarding PCR and related amplification methods and one of skill will appreciate that essentially any RNA can be converted into a double stranded DNA suitable for restriction digestion, PCR expansion and sequencing using reverse transcriptase and a polymerase.

PCR detection and quantification using dual-labeled fluorogenic oligonucleotide probes, commonly referred to as "TaqMan™" probes, can also be performed according to the present invention. These probes are composed of short (e.g., 20-25 base) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. TaqMan™ probes are oligonucleotides that have a label and a quencher, where the label is released during amplification by the exonuclease action of the polymerase used in amplification, providing a real time measure of amplification during synthesis. A variety of TaqMan™ reagents are commercially available, e.g., from Applied Biosystems as well as from a variety of specialty vendors such as Biosearch Technologies.

In one embodiment, the presence or absence of a molecular marker is determined simply through nucleotide sequencing of the polymorphic marker region. This method is readily adapted to high throughput analysis as are the other methods noted above, e.g., using available high throughput sequencing methods such as sequencing by hybridization.

In alternative embodiments, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST® (basic local alignment search tool), or even simple word processors.

While the exemplary markers provided in the figures and tables herein are either SNP markers, any of the aforementioned marker types can be employed in the context of the invention to identify chromosome intervals encompassing genetic element that contribute to superior agronomic performance (e.g., drought tolerance or improved drought tolerance).

Probes and Primers

In general, synthetic methods for making oligonucleotides, including probes, primers, molecular beacons, PNAs, LNAs (locked nucleic acids), etc., are well known. For example, oligonucleotides can be synthesized chemically according to the solid phase phosphoramidite triester method described. Oligonucleotides, including modified oligonucleotides, can also be ordered from a variety of commercial sources.

Nucleic acid probes to the marker loci can be cloned and/or synthesized. Any suitable label can be used with a probe of the invention. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radio labels, enzymes, and colorimetric labels. Other labels include ligands which bind to antibodies labeled with fluorophores, chemiluminescent agents, and enzymes. A probe can also constitute radio labeled PCR primers that are used to generate a radio labeled amplicon.

It is not intended that the nucleic acid probes of the invention be limited to any particular size.

In some preferred embodiments, the molecular markers of the invention are detected using a suitable PCR-based detection method, where the size or sequence of the PCR amplicon is indicative of the absence or presence of the marker (e.g., a particular marker allele). In these types of methods, PCR primers are hybridized to the conserved regions flanking the polymorphic marker region. As used in the art, PCR primers used to amplify a molecular marker are sometimes termed "PCR markers" or simply "markers." It will be appreciated that, although many specific examples of primers are provided herein, suitable primers to be used with the invention can be designed using any suitable method. It is not intended that the invention be limited to any particular primer or primer pair. In some embodiments, the primers of the invention are radiolabelled, or labeled by any suitable means (e.g., using a non-radioactive fluorescent tag), to allow for rapid visualization of the different size amplicons following an amplification reaction without any additional labeling step or visualization step. In some embodiments, the primers are not labeled, and the amplicons are visualized following their size resolution, e.g., following agarose gel electrophoresis. In some embodiments, ethidium bromide staining of the PCR amplicons following size resolution allows visualization of the different size amplicons. It is not intended that the primers of the invention be limited to generating an amplicon of any particular size. For example, the primers used to amplify the marker loci and alleles herein are not limited to amplifying the entire region of the relevant locus. The primers can generate an amplicon of any suitable length that is longer or shorter than those disclosed herein. In some embodiments, marker amplification produces an amplicon at least 20 nucleotides in length, or alternatively, at least 50 nucleotides in length, or alternatively, at least 100 nucleotides in length, or alternatively, at least 200 nucleotides in length. Marker alleles in addition to those recited herein also find use with the present invention.

Linkage Analysis and QTL

Linkage Analysis

"Linkage", or "genetic linkage," is used to describe the degree with which one marker locus is "associated with" another marker locus or some other locus (for example, a tolerance locus). For example, if locus A has genes "A" or "a" and locus B has genes "B" or "b", a cross between parent 1 with AABB and parent 2 with aabb will produce four possible gametes wherein the genes are segregated as AB, Ab, aB and ab. The null expectation is that there will be independent equal segregation into each of the four possible genotypes, i.e. with no linkage ¼ of the gametes will of each genotype. Segregation of gametes into a genotypes differing from ¼ is attributed to linkage. As used herein, linkage can be between two markers, or alternatively between a marker and a phenotype. A marker locus can be associated with (linked to) a trait, e.g., a marker locus can be associated with tolerance or improved tolerance to a plant pathogen when the marker locus is in linkage disequilibrium with the tolerance trait. The degree of linkage of a molecular marker to a phenotypic trait (e.g., a QTL) is measured, e.g., as a statistical probability of co-segregation of that molecular marker with the phenotype.

As used herein, the linkage relationship between a molecular marker and a phenotype is the statistical likelihood that the particular combination of a phenotype and the presence or absence of a particular marker allele is random. Thus, the lower the probability score, the greater the likelihood that a phenotype and a particular marker will cosegregate. In some embodiments, a probability score of 0.05 (p=0.05, or a 5% probability) of random assortment is considered a significant indication of co-segregation. However, the present invention is not limited to this particular standard, and an acceptable probability can be any probability of less than 50% (p<0.5). For example, a significant probability can be less than 0.25, less than 0.20, less than 0.15, or less than 0.1. The phrase "closely linked," in the present application, means that recombination between two linked loci occurs with a frequency of equal to or less than about 20% (i.e., are separated on a genetic map by not more than 20 cM). In one aspect, any marker of the invention is linked (genetically and physically) to any other marker that is at or less than 50 cM distant. In another aspect, any marker of the invention is closely linked (genetically and physically) to any other marker that is in close proximity, e.g., at or less than about 20 cM distant. Two closely linked markers on the same chromosome, for example, the markers and loci identified in Tables 1-2, can be positioned about 20, 19, 18, 17, 16, 15, 14, 13, 12, 11, 10, 9, 8, 7, 6, 5, 4, 3, 2, 1, 0.75, 0.5 or 0.25 cM or less from each other.

Classical linkage analysis can be thought of as a statistical description of the relative frequencies of cosegregation of different traits. Linkage analysis is the well characterized descriptive framework of how traits are grouped together based upon the frequency with which they segregate together. That is, if two non-allelic traits are inherited together with a greater than random frequency, they are said to be "linked." The frequency with which the traits are inherited together is the primary measure of how tightly the traits are linked, i.e., traits which are inherited together with a higher frequency are more closely linked than traits which are inherited together with lower (but still above random) frequency. The further apart on a chromosome the genes reside, the less likely they are to segregate together, because homologous chromosomes recombine during meiosis. Thus, the further apart on a chromosome the genes reside, the more likely it is that there will be a crossing over event during meiosis that will result in the marker and the DNA sequence responsible for the trait the marker is designed to track segregating separately into progeny. A common measure of linkage is the frequency with which traits cosegregate. This can be expressed as a percentage of cosegregation (recombination frequency) or, also commonly, in centiMorgans (cM).

Linkage analysis is used to determine which polymorphic marker allele demonstrates a statistical likelihood of cosegregation with the tolerance phenotype (thus, a "tolerance marker allele"). Following identification of a marker allele for cosegregation with the tolerance phenotype, it is possible to use this marker for rapid, accurate screening of plant lines for the tolerance allele without the need to grow the plants through their life cycle and await phenotypic evaluations, and furthermore, permits genetic selection for the particular tolerance allele even when the molecular identity of the actual tolerance QTL is unknown. Tissue samples can be taken, for example, from the endosperm, embryo, or mature/developing plant and screened with the appropriate molecular marker to rapidly determine which progeny contain the desired genetics. Linked markers also remove the impact of environmental factors that can often influence phenotypic expression.

Because chromosomal distance is approximately proportional to the frequency of crossing over events between traits, there is an approximate physical distance that correlates with recombination frequency. Marker loci are themselves traits and can be assessed according to standard linkage analysis by tracking the marker loci during segregation. Thus, in the context of the present invention, one cM is equal to a 1% chance that a marker locus will be separated from another locus (which can be any other trait, e.g., another marker locus, or another trait locus that encodes a QTL), due to crossing over in a single generation.

When referring to the relationship between two genetic elements, such as a genetic element contributing to tolerance and a proximal marker, "coupling" phase linkage indicates the state where the "favorable" allele at the tolerance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for tolerance) is physically linked with an "unfavorable" allele at the proximal marker locus, and the two "favorable" alleles are not inherited together (i.e., the two loci are "out of phase" with each other).

Quantitative Trait Loci

An allele of a QTL can comprise multiple genes or other genetic factors even within a contiguous genomic region or linkage group, such as a haplotype. As used herein, an allele of a drought tolerance locus can encompass more than one gene or nucleotide sequence where each individual gene or nucleotide sequence is also capable of exhibiting allelic variation and where each gene or nucleotide sequence is also capable of eliciting a phenotypic effect on the quantitative trait in question. In an aspect of the present invention the allele of a QTL comprises one or more genes or nucleic acid sequences that are also capable of exhibiting allelic variation. The use of the term "an allele of a QTL" is thus not intended to exclude a QTL that comprises more than one gene or other genetic factor. Specifically, an "allele of a QTL" in the present in the invention can denote a haplotype within a haplotype window wherein a phenotype can be drought tolerance. A haplotype window is a contiguous genomic region that can be defined, and tracked, with a set of one or more polymorphic markers wherein the polymorphisms indicate identity by descent. A haplotype within that window can be defined by the unique fingerprint of alleles at each marker. As used herein, an allele is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus. Plants of the present invention may be homozygous or heterozygous at any particular drought locus or for a particular polymorphic marker.

The principles of QTL analysis and statistical methods for calculating linkage between markers and useful QTL, or between any loci in a genome are well known in the art. Exemplary methods include penalized regression analysis, ridge regression, single point marker analysis, complex pedigree analysis, Bayesian MCMC, identity-by-descent analysis, interval mapping, composite interval mapping, and Haseman-Elston regression. QTL analyses are often performed with the help of a computer and specialized software available from a variety of public and commercial sources known to those of skill in the art.

Genetic Mapping

A "genetic map" is the relationship of genetic linkage among loci on one or more chromosomes (or linkage groups) within a given species, generally depicted in a diagrammatic or tabular form. "Genetic mapping" is the process of defining the linkage relationships of loci through the use of genetic markers, populations segregating for the markers, and standard genetic principles of recombination frequency. A "genetic map location" is a location on a genetic map relative to surrounding genetic markers on the same linkage group where a specified marker can be found within a given species. In contrast, a physical map of the genome refers to absolute distances (for example, measured in base pairs or isolated and overlapping contiguous genetic fragments, e.g., contigs). A physical map of the genome does not take into account the genetic behavior (e.g., recombination frequencies) between different points on the physical map. A "genetic recombination frequency" is the frequency of a crossing over event (recombination) between two genetic loci. Recombination frequency can be observed by following the segregation of markers and/or traits following meiosis. In some cases, two different markers can have the same genetic map coordinates. In that case, the two markers are in such close proximity to each other that recombination occurs between them with such low frequency that it is undetected.

Genetic maps are graphical representations of genomes (or a portion of a genome such as a single chromosome) where the distances between markers are measured by the recombination frequencies between them. Plant breeders use genetic maps of molecular markers to increase breeding efficiency through marker assisted selection (MAS), a process where selection for a trait of interest is not based on the trait itself but rather on the genotype of a marker linked to the trait. A molecular marker that demonstrates reliable linkage with a phenotypic trait provides a useful tool for indirectly selecting the trait in a plant population, especially when accurate phenotyping is difficult, slow, or expensive.

In general, the closer two markers or genomic loci are on the genetic map, the closer they lie to one another on the physical map. A lack of precise proportionality between cM distances and physical distances can exist due to the fact that the likelihood of genetic recombination is not uniform throughout the genome; some chromosome regions are cross-over "hot spots," while other regions demonstrate only rare recombination events, if any.

Genetic mapping variability can also be observed between different populations of the same crop species. In spite of this variability in the genetic map that may occur between populations, genetic map and marker information derived from one population generally remains useful across multiple populations in identification of plants with desired traits, counter-selection of plants with undesirable traits and in guiding MAS.

As one of skill in the art will recognize, recombination frequencies (and as a result, genetic map positions) in any particular population are not static. The genetic distances separating two markers (or a marker and a QTL) can vary depending on how the map positions are determined. For example, variables such as the parental mapping populations used, the software used in the marker mapping or QTL mapping, and the parameters input by the user of the mapping software can contribute to the QTL marker genetic map relationships. However, it is not intended that the invention be limited to any particular mapping populations, use of any particular software, or any particular set of software parameters to determine linkage of a particular marker or chromosome interval with the drought tolerance phenotype. It is well within the ability of one of ordinary skill in the art to extrapolate features described herein to any gene pool or population of interest, and using any particular software and software parameters. Indeed, observations regarding genetic markers and chromosome intervals in populations in addition to those described herein are readily made using the teaching of the present disclosure.

Association Mapping

Association or LD mapping techniques aim to identify genotype-phenotype associations that are significant. It is effective for fine mapping in outcrossing species where frequent recombination among heterozygotes can result in rapid LD decay. LD is non-random association of alleles in a collection of individuals, reflecting the recombinational history of that region. Thus, LD decay averages can help determine the number of markers necessary for a genome-wide association study to generate a genetic map with a desired level of resolution.

Large populations are better for detecting recombination, while older populations are generally associated with higher levels of polymorphism, both of which contribute to accelerated LD decay. However, smaller effective population sizes tend to show slower LD decay, which can result in more extensive haplotype conservation. Understanding of the relationships between polymorphism and recombination is useful in developing strategies for efficiently extracting information from these resources. Association analyses compare the plants' phenotypic score with the genotypes at the various loci. Subsequently, any suitable maize genetic map (for example, a composite map) can be used to help observe distribution of the identified QTL markers and/or QTL marker clustering using previously determined map locations of the markers.

Marker Assisted Selection, Plant Breeding, and Genomic Introgression

Marker Assisted Selection

"Introgression" refers to the transmission of a desired allele of a genetic locus from one genetic background to another by. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background.

A primary motivation for development of molecular markers in crop species is the potential for increased efficiency in plant breeding through marker assisted selection (MAS). Genetic markers are used to identify plants that contain a desired genotype at one or more loci, and that are expected to transfer the desired genotype, along with a desired phenotype to their progeny. Genetic markers can be used to identify plants containing a desired genotype at one locus, or at several unlinked or linked loci (e.g., a haplotype), and that would be expected to transfer the desired genotype, along with a desired phenotype to their progeny. The present invention provides the means to identify plants that are tolerant, exhibit improved tolerance or are susceptible to low water growth conditions by identifying plants having a specified allele that is linked to csd1 or csd2.

In general, MAS uses polymorphic markers that have been identified as having a significant likelihood of cosegregation with a tolerance trait. Such markers are presumed to map near a gene or genes that give the plant its tolerance phenotype, and are considered indicators for the desired trait, and are termed QTL markers. Plants are tested for the presence or absence of a desired allele in the QTL marker.

Identification of plants or germplasm that include a marker locus or marker loci linked to a tolerance trait or traits provides a basis for performing marker assisted selection. Plants that comprise favorable markers or favorable alleles are selected for, while plants that comprise markers or alleles that are negatively correlated with tolerance can be selected against. Desired markers and/or alleles can be introgressed into plants having a desired (e.g., elite or exotic) genetic background to produce an introgressed tolerant plant or germplasm. In some aspects, it is contemplated that a plurality of tolerance markers are sequentially or simultaneously selected and/or introgressed. The combinations of tolerance markers that are selected for in a single plant is not limited, and can include any combination of markers disclosed herein or any marker linked to the markers disclosed herein, or any markers located within the QTL intervals defined herein.

In some embodiments, the allele that is detected is a favorable allele that positively correlates with drought tolerance or improved drought tolerance. In the case where more than one marker is selected, an allele is selected for each of the markers; thus, two or more alleles are selected. In some embodiments, it can be the case that a marker locus will have more than one advantageous allele, and in that case, either allele can be selected. It will be appreciated that the ability to identify QTL marker loci alleles that correlate with tolerance, improved tolerance or susceptibility of a corn plant to drought conditions provides a method for selecting plants that have favorable marker loci as well. That is, any plant that is identified as comprising a desired marker locus (e.g., a marker allele that positively correlates with tolerance) can be selected for, while plants that lack the locus, or that have a locus that negatively correlates with tolerance, can be selected against.

In some embodiments, a drought tolerant first corn plant or germplasm (the donor) can be crossed with a second corn plant or germplasm (the recipient, e.g., an elite or exotic corn, depending on characteristics that are desired in the progeny) to create an introgressed corn plant or germplasm as part of a breeding program designed to improve drought tolerance of the recipient corn plant or germplasm. In some aspects, the recipient plant can also contain one or more drought tolerant loci, which can be qualitative or quantitative trait loci. In another aspect, the recipient plant can contain a transgene.

In some embodiments, the recipient corn plant or germplasm will typically display reduced tolerance to drought conditions as compared to the first corn plant or germplasm, while the introgressed corn plant or germplasm will display an increased tolerance to drought conditions as compared to the second plant or germplasm. An introgressed corn plant or germplasm produced by these methods are also a feature of this invention.

MAS is a powerful shortcut to selecting for desired phenotypes and for introgressing desired traits into cultivars (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

When a population is segregating for multiple loci affecting one or multiple traits, e.g., multiple loci involved in tolerance, or multiple loci each involved in tolerance or tolerance to different diseases or environmental conditions, the efficiency of MAS compared to phenotypic screening becomes even greater, because all of the loci can be evaluated in the lab together from a single sample of DNA.

Marker Assisted Backcrossing

One application of MAS is to use the tolerance or improved tolerance markers to increase the efficiency of an introgression effort aimed at introducing a tolerance QTL into a desired (typically high yielding) background. If the nucleic acids from a plant are positive for a desired genetic marker allele, the plant can be self fertilized to create a true breeding line with the same genotype, or it can be crossed with a plant with the same marker or with other characteristics to create a sexually crossed hybrid generation.

Another use of MAS in plant breeding is to assist the recovery of the recurrent parent genotype by backcross breeding. Backcross breeding is the process of crossing a progeny back to one of its parents or parent lines. Backcrossing is usually done for the purpose of introgressing one or a few loci from a donor parent (e.g., a parent comprising desirable tolerance marker loci) into an otherwise desirable genetic background from the recurrent parent (e.g., an otherwise high yielding line). The more cycles of back crossing that are done, the greater the genetic contribution of the recurrent parent to the resulting introgressed variety. This is often necessary, because tolerant plants may be otherwise undesirable, e.g., due to low yield, low fecundity, or the like. In contrast, lines which are the result of intensive breeding programs may have excellent yield, fecundity or the like, merely being deficient in one desired trait such as tolerance to low water growth conditions.

Moreover, in another aspect, while maintaining the introduced markers associated with tolerance, the genetic contribution of the plant providing drought tolerance can be reduced by back-crossing or other suitable approaches. In one aspect, the nuclear genetic material derived from the donor material in the plant can be less than or about 50%, less than or about 25%, less than or about 13%, less than or about 5%, 3%, 2% or 1%, but that the recipient remains resistant to drought.

Genetic diversity is important for long term genetic gain in any breeding program. With limited diversity, genetic gain will eventually plateau when all of the favorable alleles have been fixed within the elite population. One objective is to incorporate diversity into an elite pool without losing the genetic gain that has already been made and with the minimum possible investment. MAS provide an indication of which genomic regions and which favorable alleles from the original ancestors have been selected for and conserved over time, facilitating efforts to incorporate favorable variation from exotic germplasm sources (parents that are unrelated to the elite gene pool) in the hopes of finding favorable alleles that do not currently exist in the elite gene pool.

Transgenic Uses of Csd1 and Csd2 to Alter Drought Tolerance.

As an alternative to standard breeding methods of introducing traits of interest (e.g., introgression), transgenic approaches can also be used. In these methods, exogenous nucleic acids that encode traits linked to markers are introduced into target plants or germplasm. For example, a nucleic acid that codes for a tolerance trait is cloned, e.g., via positional cloning and introduced into a target plant or germplasm. Certain aspects of this embodiment of the invention provide transgenic plant cells having stably integrated recombinant DNA constructs, transgenic plants and seeds comprising a plurality of such transgenic plant cells and transgenic pollen of such plants.

Embodiments of the invention also provide methods for manufacturing transgenic seed that can be used to produce a crop of transgenic plants with an enhanced trait resulting from expression of a stably-integrated recombinant DNA construct. The methods may comprise one or more of the following steps: (a) screening a population of plants for an enhanced trait and a recombinant DNA construct, where individual plants in the population can exhibit the trait at a level less than, essentially the same as, or greater than the level that the trait is exhibited in control plants, (b) selecting from the population one or more plants that exhibit the trait at a level greater than the level that said trait is exhibited in control plants, (c) collecting seed from a selected plant, (d) verifying that the recombinant DNA is stably integrated in said selected plants, (e) analyzing tissue of a selected plant to detect the production level of a protein having the function of a protein encoded by nucleotides in at least one sequence selected from SEQ ID NOs: 1 or 2.

Another embodiment of this invention is a transcribable polynucleotide molecule, such as those provided as SEQ ID NOs: 1 or 2, operably linked to a promoter polynucleotide molecule so as to modulate transcription of the transcribable polynucleotide molecule at a desired level or in a desired pattern upon introduction of said construct into a plant cell. In one embodiment, the transcribable polynucleotide molecule comprises a protein-coding region of a gene, and the promoter affects the transcription of an RNA molecule that is translated and expressed as a protein product. In another embodiment, the transcribable polynucleotide molecule includes, but not limited to, an antisense region of a gene, and the promoter affects the transcription of an antisense RNA molecule or other similar inhibitory RNA molecule in order to inhibit expression of a specific RNA molecule of interest in a target host cell.

Recombinant DNA constructs are assembled using methods well known to persons of ordinary skill in the art and typically comprise a promoter operably linked to DNA, the expression of which provides the enhanced agronomic trait. Other construct components can include additional regulatory elements, such as 5' leaders and introns for enhancing transcription, 3' untranslated regions (such as polyadenylation signals and sites), DNA for transit or signal peptides.

Numerous promoters that are active in plant cells have been described in the literature. These include promoters present in plant genomes as well as promoters from other sources, including nopaline synthase (NOS) promoter and octopine synthase (OCS) promoters carried on tumor-inducing plasmids of *Agrobacterium tumefaciens* and the CaMV35S promoters from the cauliflower mosaic virus as well as other promoters derived from plant genes.

Recombinant DNA constructs for gene suppression can be designed for any of the well-known methods for suppressing transcription of a gene, the accumulation of the mRNA corresponding to that gene or preventing translation of the transcript into protein. Posttranscriptional gene suppression can be practically effected by transcription of RNA that forms double-stranded RNA (dsRNA) having homology to mRNA produced from a gene targeted for suppression.

Transgenic plants comprising or derived from plant cells of this invention transformed with recombinant DNA described in this invention can be further enhanced with stacked traits, e.g. a crop plant having an enhanced trait resulting from expression of DNA disclosed herein in combination with herbicide and/or pest tolerance traits.

Aspects of the various embodiments of the invention also provide for nucleic acid fragments of SEQ ID NOs: 1-2.

Other aspects of the various embodiments of the invention include transgenic plants, transgenic plant seeds, transgenic crops, plant products and byproducts having any of the nucleic acid or protein fragments described above. The invention also provides for various methods that use such fragments.

Embodiments of the present invention also contemplate that the trait-improving recombinant DNA provided herein can be used in combination with other recombinant DNA to create plants with multiple desired traits or a further enhanced trait. The combinations generated can include multiple copies of any one or more of the recombinant DNA constructs. These stacked combinations can be created by any method, including but not limited to, cross breeding of transgenic plants or multiple genetic transformations.

In addition to direct transformation of a plant material with a recombinant DNA, a transgenic plant cell nucleus can be prepared by crossing a first plant having cells with a transgenic nucleus with recombinant DNA with a second plant lacking the transgenic nucleus. Progeny can be recovered from transformed plants and tested for expression of the transgenic recombinant polynucleotide.

Although the plant cells and methods of this invention can be applied to any plant cell, plant, seed or pollen, e.g. any fruit, vegetable, grass, tree or ornamental plant, the various aspects of the invention are preferably applied to corn, soybean, cotton, canola, alfalfa, wheat, rice, sugarcane, and sugar beet plants. In many cases the invention is applied to one or more corn plants that already possess some form of drought tolerance to further enhance their ability to resist drought conditions.

In certain embodiment, the present invention also includes identification of homologs of proteins encoded by the DNA identified in the sequence listing which is used to provide transgenic seed and plants having enhanced agronomic traits. From the sequence of the homologs, homologous DNA sequence are identified for preparing additional transgenic seeds and plants of this invention with enhanced agronomic traits.

A drought tolerance locus or allele at that locus may be introduced into any plant that also contains any number or combination of additional transgenic traits. Non-limiting examples of transgenic traits comprise herbicide tolerance, increased yield, insect control, fungal disease tolerance, virus tolerance, nematode tolerance, bacterial disease tolerance, *mycoplasma* disease tolerance, modified oil production, high oil production, high protein production, germination and seedling growth control, enhanced animal and human nutrition, low raffinose, environmental stress resistant, increased digestibility, industrial enzymes, pharmaceutical proteins, peptides and small molecules, improved processing traits, improved flavor, nitrogen fixation, hybrid seed production, reduced allergenicity, biopolymers, and biofuels among others. In one aspect, the herbicide tolerance is selected from the group consisting of glyphosate, dicamba, glufosinate, sulfonylurea, bromoxynil and norflurazon herbicides. These traits can be provided by methods of plant biotechnology as transgenes in corn.

Recombinant DNA constructs can be prepared using the DNA encoding each of the identified homologs and the constructs can be used to prepare multiple events of transgenic corn, soybean, canola, cotton and other transgenic plants mentioned. Plants can be regenerated from the transformed plant cells and used to produce progeny plants and seed that are screened for enhanced water use efficiency, enhanced cold tolerance, increased yield, enhanced nitrogen use efficiency, enhanced seed protein and enhanced seed oil. From each group of multiple events of transgenic plants with a specific recombinant DNA for a homolog the event that produces the greatest enhancement in yield, water use efficiency, nitrogen use efficiency, enhanced cold tolerance, enhanced seed protein and enhanced seed oil is identified and progeny seed can be selected for commercial development.

Modification of the Location, Copy Number, or Expression of Csd1 or Csd2 to Alter Drought Tolerance.

It is anticipated that one skilled in the art could modify drought tolerance in a plant by altering the expression of the csd1 or csd2 gene sequences disclosed herein (SEQ ID NO: 1 or SEQ ID NO: 2, respectively) using one or more methods known in the art.

One method of altering the expression of these genes could be by targeted recombination of csd1 or csd2 into specific locations of the corn genome, or by targeted recombination of other sequences that modify the expression of csd1 or csd2. This can be achieved using endonucleases or other double-strand break inducing agents.

In one embodiment, at least one plant cell is obtained comprising at least one recognition sequence for a custom endonuclease, wherein the custom endonuclease is a fusion protein and the fusion protein comprises a zinc finger DNA binding domain or a Vir protein domain. Further, the custom endonuclease can comprise a polypeptide, a catalytically active RNA, an RNA-directed endonuclease, or a synthetic aptamer. The custom endonuclease can, for instance, be a meganuclease and the DNA encoding the nuclease can be expressed in the plant cell under the control of a constitutive, inducible, or tissue-specific promoter.

The plant cell can further comprise a second exogenous custom endonuclease, wherein the first and the second exogenous custom endonuclease each comprise different recognition sequences within the genome of the plant cell and are capable of producing a cut proximal to said recognition sequences.

The csd1 or csd2 locus can be modified by introducing into a plant cell at least a first custom endonuclease, wherein the cell comprises a recognition sequence for the custom endonuclease in or proximal to the csd1 or csd2 locus; allowing the custom endonuclease to create a double stranded break in the DNA making up or flanking csd1 or csd2; and identifying the cell or a progeny cell thereof as comprising a modification in said locus of interest.

These methods of site-directed recombination used to modify csd1 or csd2 can comprise gene conversion, gene replacement, homologous recombination, heterologous recombination, targeted insertion, a deletion, or homeologous recombination and wherein the modification alters the expression of csd1 or csd2, or otherwise results in altered tolerance to drought.

Other ways to improve drought tolerance of a plant using the csd1 or csd2 gene sequences comprise insertion of transgenic versions of the genes, insertion of a vector stack of transgenes that comprises the csd1 or csd2 sequences, insertion of a different nucleic acid of interest proximal to the csd1 or csd2 loci in the corn genome, or insertion of a different nucleic acid of interest preceding, following, or simultaneous to excision of csd1 or csd2 in the corn genome. This capability allows custom stacking of at least one sequence in addition to the csd1 or csd2 genes as well as the ability to test for performance of one or more nucleic acids of interest, which may comprise alternative expression designs for the csd1 or csd2 loci. These methods can be used to test the performance of csd1 or csd2 variants at different locations in the corn genome.

Additionally, endogenous copies of the coding sequences of csd1 or csd2 may be replaced by variants coding sequences of the genes that have optimized codons, or coding sequences encoding variant polypeptides with improved or altered protein or enzymatic activities may replace the versions of the genes previously found in the genome of a plant. For instance, variant gene sequences of csd1 or csd2 obtained by in vitro mutagenesis, or polypeptides encoded by different alleles of the genes, or homologs of the genes, or alternative domain splice variants of the encoding polypeptides, or related genes in the same gene family as csd1 or csd2 may be utilized. Similar methods known in the art could be used to shuffle the various domains of the polypeptides encoded by csd1 or csd2 in order to create domain combinations which improve drought tolerance in the plant.

Custom stacking the csd1 or csd2 genes with one or more other desired sequences is another potential embodiment of this invention. This stacking can take place in the genome of the plant and can include sequence configurations relative to one another that increase transformation and/or expression efficiency and/or otherwise improve expression control.

Supernumerary chromosomes could serve as sites of csd1 or csd2 insertion. Expression of csd1 or csd2 sequences, or close variants, could be directed from such supernumerary chromosomes, using additional regulatory elements known in the art to alter the ability of a plant to resist drought infection.

Alternatively, recombination-inducing elements other than endonucleases known in the art, such as ultraviolet light, X-rays, stress, or various chemicals, could be used to create variants of the csd1 or csd2 sequences, or they could be used to change the location of the csd1 or csd2 genes in the corn genome, or even to add additional copies or variants of the genes to other locations, including supernumerary chromosomes. Additional copies of the genes, or variants of them, could even be stacked at or adjacent to the endogenous csd1 or csd2 loci. Such methods could also be employed to convert csd1 or csd2 in the genome from susceptible versions into alleles encoding improved drought tolerance.

Methods for modifying drought tolerance by altering a sequence known to regulate csd1 or csd2 expression are well known in the art. Such regulator sequences comprise enhancer elements, suppressor elements, 5'-UTR, 3'-UTR, promoters, and introns that lead to the desired expression pattern, such as those from different alleles or homologs of csd1 or csd2, or from other genes with the desired expression patterns. The modification can alter the expression level or expression pattern of csd1 or csd2 either alone or in combination with altering the expression of a second gene involved in a biochemical pathway.

Furthermore, an enhancer or suppressor element can be introduced into the promoter or UTR region of a gene of interest at its native genomic location in order to alter gene expression level without changing the expression pattern. For example, an enhancer or suppressor element, such as the HSP70 intron, or other cis-acting element, such as the Akadis enhancer element, is introduced into the regulatory regions of csd1 or csd2, such as the UTR region or the promoter region of the native wild-type gene. Because these enhancer elements can change the expression level while maintaining the expression pattern, the resulting transgenic plants would be expected to have increased csd1 or csd2 expression level without substantially changing the native expression pattern of those genes.

Since biological pathways are typically controlled by both positive and negative regulators, improved drought tolerance might be achieved by over-expressing the positive regulator and the knock out of the negative regulator at the same time, and in a controlled (i.e. a cell-type-specific or tissue-specific manner). For example, the coding sequence for a positive regulator of csd1 or csd2 can be introduced into the locus of the negative regulator of those genes, resulting in transgenic plants that express the positive regulator driven by the promoter of the negative regulator, resulting in increased expression from the native locus of csd1 or csd2.

Methods described in the art permit the creation of plants which comprise regulatory elements that can be induced to activate, inhibit, or eliminate at least copy or coding variant of csd1 or csd2 in response to one or more external stimuli. For example, a transgenic version of csd1 or csd2 could be engineered in a plant cell with a chemically inducible promoter, such as glyphosate, wherein activation or inhibition of csd1 or csd2 could be controlled by application of that specific chemical. The transgene and its promoter can be integrated in the genome or on an extrachromosomal element or a supernumerary chromosome. Upon application of the specific chemical to the plant, the inducible promoter is expressed such that it activates or inhibits at least one copy of csd1 or csd2. With this technology, the grower has the potential to make real time decisions in response to potential or actual exposure of crops to drought.

It is anticipated that one skilled in the art could use any of the methods described herein to modify drought tolerance, or the expression of csd1 or csd2, in other plant species, especially crops with agricultural value.

General Terms and Definitions

Systems, including automated systems for selecting plants that comprise a marker of interest and/or for correlating presence of the marker with tolerance are also a feature of the invention. These systems can include probes relevant to marker locus detection, detectors for detecting labels on the probes, appropriate fluid handling elements and temperature controllers that mix probes and templates and/or amplify templates, and systems instructions that correlate label detection to the presence of a particular marker locus or allele.

In an aspect, this invention could be used on any plant. In another aspect, the plant is selected from the genus *Zea*. In another aspect, the plant is selected from the species *Zea mays*. In a further aspect, the plant is selected from the subspecies *Zea mays* L. ssp. *mays*. In an additional aspect, the plant is selected from the group *Zea mays* L. subsp. *mays* Indentata, otherwise known as dent corn. In another aspect, the plant is selected from the group *Zea mays* L. subsp. *mays* Indurata, otherwise known as flint corn. In an aspect, the plant is selected from the group *Zea mays* L. subsp. *mays*

Saccharata, otherwise known as sweet corn. In another aspect, the plant is selected from the group *Zea mays* L. subsp. *mays* Amylacea, otherwise known as flour corn. In a further aspect, the plant is selected from the group *Zea mays* L. subsp. *mays* Everta, otherwise known as pop corn. *Zea* plants include hybrids, inbreds, partial inbreds, or members of defined or undefined populations.

In a preferred aspect, the present invention provides a plant to be assayed for tolerance or susceptibility to drought by any method to determine whether a plant is resistant, susceptible, or whether it exhibits some degree of tolerance or susceptibility. Populations of plants can be similarly characterized in this manner, or further characterized as segregating for the trait of drought tolerance.

It is further understood that a plant of the present invention may exhibit the characteristics of any relative maturity group. In an aspect, the maturity group is selected from the group consisting of early maturing varieties, mid season maturing varieties, and full season varieties.

The present invention also provides for parts of the plants of the present invention. Plant parts, without limitation, include seed, endosperm, ovule and pollen. In a particularly preferred aspect of the present invention, the plant part is a seed.

In another aspect, the corn seed can be subjected to various treatments. For example, the seeds can be treated to improve germination by priming the seeds or by disinfection to protect against seed-born pathogens. In another aspect, seeds can be coated with any available coating to improve, for example, plantability, seed emergence, and protection against seed-born pathogens. Seed coating can be any form of seed coating including, but not limited to, pelleting, film coating, and encrustments.

It is further understood, that the present invention provides bacterial, viral, microbial, insect, mammalian and plant cells comprising the nucleic acid molecules of the present invention.

In another aspect, the corn plant can show a comparative tolerance compared to a non-resistant control corn plant. In this aspect, a control corn plant will preferably be genetically similar except for the drought tolerance allele or alleles in question. Such plants can be grown under similar conditions with equivalent or near equivalent exposure to the pathogen.

Various patent and non-patent publications are cited herein, the disclosures of each of which are incorporated herein by reference in their entireties.

As various modifications could be made in the constructions and methods herein described and illustrated without departing from the scope of the invention, it is intended that all matter contained in the foregoing description or shown in the accompanying drawings shall be interpreted as illustrative rather than limiting. The breadth and scope of the present invention should not be limited by any of the above-described exemplary embodiments, but should be defined only in accordance with the following claims appended hereto and their equivalents.

Descriptions of commonly used breeding terms and methods for crossing and producing hybrids that are used to describe present invention can be found in one of several reference books (Allard, "Principles of Plant Breeding," John Wiley & Sons, NY, U. of CA, Davis, Calif., 50-98, 1960; Simmonds, "Principles of crop improvement," Longman, Inc., NY, 369-399, 1979; Sneep and Hendriksen, "Plant breeding perspectives," Wageningen (ed), *Center for Agricultural Publishing and Documentation*, 1979; Fehr, In: Soybeans: Improvement, Production and Uses, 2nd Edition, Monograph., 16:249, 1987; Fehr, "Principles of variety development," *Theory and Technique*, (Vol. 1) and *Crop Species Soybean* (Vol. 2), Iowa State Univ., Macmillan Pub. Co., NY, 360-376, 1987).

The definitions and methods provided define the present invention and guide those of ordinary skill in the art in the practice of the present invention. Unless otherwise noted, terms are to be understood according to conventional usage by those of ordinary skill in the relevant art. Examples of resources describing many of the terms related to molecular biology used herein can be found in Alberts et al., Molecular Biology of The Cell, 5$^{th}$ Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed, Oxford University Press: New York, 2002; and Lewin, Genes Icorn, Oxford University Press: New York, 2007. The nomenclature for DNA bases as set forth at 37 CFR § 1.822 is used.

Definitions

Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

"Adjacent", when used to describe a nucleic acid molecule that hybridizes to DNA containing a polymorphism, refers to a nucleic acid that hybridizes to DNA sequences that directly about the polymorphic nucleotide base position. For example, a nucleic acid molecule that can be used in a single base extension assay is "adjacent" to the polymorphism.

"Allele" refers to an alternative nucleic acid sequence at a particular locus; the length of an allele can be as small as 1 nucleotide base, but is typically larger. For example, a first allele can occur on one chromosome, while a second allele occurs on a second homologous chromosome, e.g., as occurs for different chromosomes of a heterozygous individual, or between different homozygous or heterozygous individuals in a population. A favorable allele is the allele at a particular locus that confers, or contributes to, an agronomically desirable phenotype, or alternatively, is an allele that allows the identification of susceptible plants that can be removed from a breeding program or planting. A favorable allele of a marker is a marker allele that segregates with the favorable phenotype, or alternatively, segregates with susceptible plant phenotype, therefore providing the benefit of identifying drought susceptible plants. A favorable allelic form of a chromosome interval is a chromosome interval that includes a nucleotide sequence that contributes to superior agronomic performance at one or more genetic loci physically located on the chromosome interval. "Allele frequency" refers to the frequency (proportion or percentage) at which an allele is present at a locus within an individual, within a line, or within a population of lines. For example, for an allele "A," diploid individuals of genotype "AA," "Aa," or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele. An allele positively correlates with a trait when it is linked to it and when presence of the allele is an indicator that the desired trait or trait form will occur in a plant comprising the allele. An allele negatively correlates with a trait when it is linked to it and when presence of the allele is an indicator that a desired trait or trait form will not occur in a plant comprising the allele.

"Crossed" or "cross" means to produce progeny via fertilization (e.g. cells, seeds or plants) and includes crosses between plants (sexual) and self fertilization (selfing).

"Elite line" means any line that has resulted from breeding and selection for superior agronomic performance. Numerous elite lines are available and known to those of skill in the art of corn breeding. An "elite population" is an assortment of elite individuals or lines that can be used to represent the state of the art in terms of agronomically superior genotypes of a given crop species, such as corn. Similarly, an "elite germplasm" or elite line of germplasm is an agronomically superior germplasm, typically derived from and/or capable of giving rise to a plant with superior agronomic performance, such as an existing or newly developed elite line of corn. In contrast, an "exotic line" or "exotic germplasm" is a line or germplasm derived from a plant not belonging to an available elite line or strain of germplasm. In the context of a cross between two plants or lines of germplasm, an exotic germplasm is not closely related by descent to the elite germplasm with which it is crossed. Most commonly, the exotic germplasm is not derived from any known elite line of a crop, but rather is selected to introduce genetic elements (typically desired alleles) into a breeding program.

"Exogenous nucleic acid" is a nucleic acid that is not native to a specified system (e.g., a germplasm, plant, variety, etc.), with respect to sequence, genomic position, or both. As used herein, the terms "exogenous" or "heterologous" as applied to polynucleotides or polypeptides typically refers to molecules that have been supplied to a biological system (e.g., a plant cell, a plant gene, a particular plant species or variety or a plant chromosome under study) and are not native to that particular biological system. The terms can indicate that the relevant material originated from a source other than a naturally occurring source, or can refer to molecules having a non-natural configuration, genetic location or arrangement of parts. In contrast, for example, a "native" or "endogenous" gene is a gene that does not contain nucleic acid elements encoded by sources other than the chromosome or other genetic element on which it is normally found in nature. An endogenous gene, transcript or polypeptide is encoded by its natural chromosomal locus, and not supplied to the cell.

"Genetic element" or "gene" refers to a heritable sequence of DNA, i.e., a genomic sequence, with functional significance. The term "gene" can also be used to refer to, e.g., a cDNA and/or an mRNA encoded by a genomic sequence, as well as to that genomic sequence.

"Genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome. A "haplotype" is the genotype of an individual at a plurality of genetic loci. Typically, the genetic loci described by a haplotype are physically and genetically linked, i.e., on the same chromosome interval. The terms "phenotype," or "phenotypic trait" or "trait" refers to one or more trait of an organism. The phenotype can be observable to the naked eye, or by any other means of evaluation known in the art, e.g., microscopy, biochemical analysis, genomic analysis, an assay for a particular disease tolerance, etc. In some cases, a phenotype is directly controlled by a single gene or genetic locus, i.e., a "single gene trait." In other cases, a phenotype is the result of several genes.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells that can be cultured into a whole plant.

"Linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of cosegregating traits, the loci that underlie the traits are in sufficient proximity to each other). Linked loci co-segregate more than 50% of the time, e.g., from about 51% to about 100% of the time. The tern "physically linked" is sometimes used to indicate that two loci, e.g., two marker loci, are physically present on the same chromosome. Advantageously, the two linked loci are located in close proximity such that recombination between homologous chromosome pairs does not occur between the two loci during meiosis with high frequency, e.g., such that linked loci cosegregate at least about 90% of the time, e.g., 91%, 92%, 93%, 94%, 95%, 96%, 97%, 98%, 99%, 99.5%, 99.75%, or more of the time.

A "Locus" is a chromosome region where a polymorphic nucleic acid, trait determinant, gene or marker is located. The loci of this invention comprise one or more polymorphisms in a population; i.e., alternative alleles are present in some individuals. A "gene locus" is a specific chromosome location in the genome of a species where a specific gene can be found.

"Marker Assay" means a method for detecting a polymorphism at a particular locus using a particular method, e.g. measurement of at least one phenotype (such as seed color, flower color, or other visually detectable trait), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc. "Marker assisted selection" (MAS) is a process by which phenotypes are selected based on marker genotypes.

"Molecular phenotype" is a phenotype detectable at the level of a population of one or more molecules. Such molecules can be nucleic acids, proteins, or metabolites. A molecular phenotype could be an expression profile for one or more gene products, e.g., at a specific stage of plant development, in response to an environmental condition or stress, etc.

"Operably linked" refers to the association of two or more nucleic acid elements in a recombinant DNA construct, e.g. as when a promoter is operably linked with DNA that is transcribed to RNA whether for expressing or suppressing a protein. Recombinant DNA constructs can be designed to express a protein which can be an endogenous protein, an exogenous homologue of an endogenous protein or an exogenous protein with no native homologue. Alternatively, recombinant DNA constructs can be designed to suppress the level of an endogenous protein, e.g. by suppression of the native gene. Such gene suppression can be effectively employed through a native RNA interference (RNAi) mechanism in which recombinant DNA comprises both sense and anti-sense oriented DNA matched to the gene targeted for suppression where the recombinant DNA is transcribed into RNA that can form a double-strand to initiate an RNAi mechanism. Gene suppression can also be effected by recombinant DNA that comprises anti-sense oriented DNA matched to the gene targeted for suppression. Gene suppression can also be effected by recombinant DNA that comprises DNA that is transcribed to a microRNA matched to the gene targeted for suppression.

"Percent identity" or "% identity" means the extent to which two optimally aligned DNA or protein segments are invariant throughout a window of alignment of components, for example nucleotide sequence or amino acid sequence. An "identity fraction" for aligned segments of a test sequence and a reference sequence is the number of identical components that are shared by sequences of the two aligned segments divided by the total number of sequence components in the reference segment over a window of alignment which is the smaller of the full test sequence or the full reference sequence.

"Phenotype" means the detectable characteristics of a cell or organism which can be influenced by genotype.

"Plant" refers to a whole plant any part thereof, or a cell or tissue culture derived from a plant, comprising any of: whole plants, plant components or organs (e.g., leaves, stems, roots, etc), plant tissues, seeds, plant cells, and/or progeny of the same. A plant cell is a biological cell of a plant, taken from a plant or derived through culture from a cell taken from a plant.

"Polymorphism" means the presence of one or more variations in a population. A polymorphism may manifest as a variation in the nucleotide sequence of a nucleic acid or as a variation in the amino acid sequence of a protein. Polymorphisms include the presence of one or more variations of a nucleic acid sequence or nucleic acid feature at one or more loci in a population of one or more individuals. The variation may comprise but is not limited to one or more nucleotide base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs), a restriction fragment length polymorphism, and a tag SNP. A genetic marker, a gene, a DNA-derived sequence, a RNA-derived sequence, a promoter, a 5' untranslated region of a gene, a 3' untranslated region of a gene, microRNA, siRNA, a tolerance locus, a satellite marker, a transgene, mRNA, ds mRNA, a transcriptional profile, and a methylation pattern may also comprise polymorphisms. In addition, the presence, absence, or variation in copy number of the preceding may comprise polymorphisms.

A "population of plants" or "plant population" means a set comprising any number, including one, of individuals, objects, or data from which samples are taken for evaluation, e.g. estimating QTL effects. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in-silico representations of the plants. The population members need not be identical to the population members selected for use in subsequent cycles of analyses or those ultimately selected to obtain final progeny plants. Often, a plant population is derived from a single biparental cross, but may also derive from two or more crosses between the same or different parents. Although a population of plants may comprise any number of individuals, those of skill in the art will recognize that plant breeders commonly use population sizes ranging from one or two hundred individuals to several thousand, and that the highest performing 5-20% of a population is what is commonly selected to be used in subsequent crosses in order to improve the performance of subsequent generations of the population.

"Resistance locus" means a locus that controls some measure of resistance or susceptibility to drought conditions. As used in the art, "resistance locus" is sometimes used interchangeably with "tolerance locus".

"Resistance allele" means the nucleic acid sequence associated with resistance to drought. As used in the art, "resistance allele" is sometimes used interchangeably with "tolerance allele".

"Recombinant" in reference to a nucleic acid or polypeptide indicates that the material (e.g., a recombinant nucleic acid, gene, polynucleotide, polypeptide, etc.) has been altered by human intervention. The term recombinant can also refer to an organism that harbors recombinant material, e.g., a plant that comprises a recombinant nucleic acid is considered a recombinant plant.

"Tolerance" or "improved tolerance" in a plant to low water conditions is an indication that the plant is less affected by drought conditions with respect to yield, survivability and/or other relevant agronomic measures, compared to a less tolerant, more "susceptible" plant. Tolerance is a relative term, indicating that a "tolerant" plant survives and/or produces better yields in drought conditions compared to a different (less tolerant) plant (e.g., a different corn line) grown in similar drought conditions. As used in the art, drought "tolerance" is sometimes used interchangeably with drought "resistance." One of skill will appreciate that plant tolerance to drought conditions varies widely, and can represent a spectrum of more-tolerant or less-tolerant phenotypes. However, by simple observation, one of skill can generally determine the relative tolerance or susceptibility of different plants, plant lines or plant families under drought conditions, and furthermore, will also recognize the phenotypic gradations of "tolerant."

"Transgenic plant" refers to a plant that comprises within its cells a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extrachromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

"Drought tolerance" describes the ability of a plant to survive with limited access to water. Drought tolerance is synonymous with the term "WUE", or water use efficiency, and is often used interchangeably in the art with "drought resistance".

"Vector" is a polynucleotide or other molecule that transfers nucleic acids between cells. Vectors are often derived from plasmids, bacteriophages, or viruses and optionally comprise parts which mediate vector maintenance and enable its intended use. A "cloning vector" or "shuttle vector" or "sub cloning vector" contains operably linked parts that facilitate subcloning steps (e.g., a multiple cloning site containing multiple restriction endonuclease sites). The term "expression vector" as used herein refers to a vector comprising operably linked polynucleotide sequences that facilitate expression of a coding sequence in a particular host organism (e.g., a bacterial expression vector or a plant expression vector).

"Yield" is the culmination of all agronomic traits as determined by the productivity per unit area of a particular plant product of commercial value. "Agronomic traits," include the underlying genetic elements of a given plant variety that contribute to yield over the course of growing season.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

EXAMPLES

Example 1. Targeting Endogenous Cold-Shock Loci as Potential Drought Tolerance-Associated Loci Two maize genes, csd1 and csd2 have been identified in the maize reference line B73. These two genes encode protein domains which share close homology to cold-shock domains of cspB. The two genes were mapped to chromosome 4 (csd1) and chromosome 10 (csd2). Robust PCR primers were designed with the selected amplicons having an average span of 570 bp. Regions −2 kb 5' of the ATG start site to +2 kb after the stop codons were then sequenced across a diverse panel of 96 drought tolerant or drought susceptible maize inbred lines using 454 sequencing technology. DNA sequence data were aligned and polymorphisms identified using standard bioinformatics tools.

Protein sequences with CSD Pfam annotations were identified and corresponding cDNA sequences were aligned and analyzed for redundancies which decreased the number of unique CSD-containing sequences. BLASTN® (nucleotide basic local alignment search tool) to Genbank cDNA was used to check for contaminant sequences other than maize and to assess actual expression of a given sequence. Two maize genes mapping to chromosome 4 (csd1) or chromosome 10 (csd2) show strong expression by Genbank cDNA blast results and Affymetrix® transcript profiling experiments. BLASTP® (protein basic local alignment search tool) results using CSD protein sequence to the Zea mays B73 (Maize) GIS all protein database show several cold-shock domain containing proteins in addition to CSD1 and CSD2. Upon further analysis, the proteins were either not expressed or atypical of plant cold-shock proteins; i.e. they do not contain glycine-rich regions and zinc fingers. The two maize cold shock domain containing proteins, CSD1 and CSD2 were identified and became the focus of inbred sequencing for haplotype analysis.

Linkage Disequilibrium (LD), in terms of $r^2$, was calculated using SAS. Association tests between haplotypes and drought phenotypes were performed using a mixed model. Both csd1 and csd2 had substantial LD decay present for 700 bp with an $r^2$=0.1. Thus, the association mapping appeared likely to approach subgene resolution.

Csd1 and csd2 were analyzed using an association approach to identify those markers affecting drought phenotypes, which could be used in maize improvement. The rapid LD decay of these two maize genes indicated they have not been a target of selection, which provides a high resolution of association at the subgene level. The significant association of non-coding regions of genes encoding maize CSD-containing proteins with drought phenotypes suggests that csd1 and csd2 impart stress tolerance. The two genes may play different roles in drought tolerance; csd1 may be involved in tolerance to drought stress during flowering whereas csd2 is likely involved in tolerance to drought stress during grainfill. Both genes appear to confer yield protection.

Example 2. Assays Useful for Detecting Drought Tolerance Genotypes

Examples of markers useful with this invention comprise the SNP markers listed in Tables 1 or 2, or any marker that maps within the chromosome intervals described herein (including the termini of the intervals), or any marker linked to those markers. Such markers can be assayed simultaneously or sequentially in a single sample or population of samples.

For convenience, primer sequences for amplifying some of the SNP marker loci linked to csd1 or csd2 (SEQ ID NO. 1 or 2, respectively) and the probes used to genotype the corresponding SNP sequences are provided in Table 2a. In a few cases, primers and probes are not available because they were generated by one of several companies that provide such services to the public. Primer and probe synthesis is also within the skill of the art once the SNP position in the corn genome is provided. One of skill in the art will also immediately recognize that other sequences to either side of the given primers can be used in place of the given primers, so long as the primers can amplify a region that includes the allele to be detected. Further, it will be appreciated that the precise probe to be used for detection can vary, e.g., any probe that can identify the region of a marker amplicon to be detected can be substituted for those examples provided herein. Also, configuration of the amplification primers and detection probes can, of course, vary. Thus, the invention is not limited to the primers, probes, or marker sequences specifically recited herein.

TABLE 2a

Primers and probes useful for detecting drought tolerance SNPs that map outside of, but are linked to, csd1 or csd2.

| SEQ ID NO. | SNP pos | Allele 1 | Allele 2 | Fwd Primer | Rev Primer | Probe 1 | Probe 2 |
|---|---|---|---|---|---|---|---|
| 3 | 152 | C | T | 21 | 36 | 51 | 66 |
| 4 | 205 | C | T | 22 | 37 | 52 | 67 |
| 5 | 157 | G | T | 23 | 38 | 53 | 68 |
| 6 | 231 | G | A | 24 | 39 | 54 | 69 |
| 7 | 189 | C | T | 25 | 40 | 55 | 70 |
| 8 | 167 | G | C | 26 | 41 | 56 | 71 |
| 9 | 154 | A | G | 27 | 42 | 57 | 72 |
| 10 | 999 | C | G | 28 | 43 | 58 | 73 |
| 11 | 171 | A | T | 29 | 44 | 59 | 74 |
| 12 | 132 | C | T | 30 | 45 | 60 | 75 |
| 13 | 237 | A | G | — | — | — | — |
| 14 | 253 | A | G | 31 | 46 | 61 | 76 |
| 15 | 231 | C | T | — | — | — | — |
| 16 | 869 | C | T | 32 | 47 | 62 | 77 |
| 17 | 296 | G | A | 33 | 48 | 63 | 78 |
| 18 | 223 | A | T | 34 | 49 | 64 | 79 |
| 19 | 125 | A | G | — | — | — | — |
| 20 | 247 | A | T | 35 | 50 | 65 | 80 |

— Sequence can be determined using routine methods.

TABLE 2b

Primers and probes useful for detecting drought tolerance SNPs that map within csd1 or csd2.

| csd1 (SEQ ID NO. 1) | | | csd2 (SEQ ID NO. 2) | | |
|---|---|---|---|---|---|
| SNP pos | Allele 1 | Allele 2 | SNP pos | Allele 1 | Allele 2 |
| 459 | A | G | 3648 | C | A |
| 466 | C | T | 3728-3729 | AA | CG |
| 504-506 | CTC | TTT | 3756 | T | A |
| 723 | A | G | 3763 | A | G |
| 763 | A | G | 3776 | A | T |
| 947 | A | G | 3799 | T | C |
| 955 | C | T | 3815 | G | A |
| 956 | C | T | 3849 | G | T |
| 956 | T | C | 3852 | A | T |
| 958 | C | T | 3860 | A | T |
| 967 | G | A | 3861-3863 | CTG | TCT |
| 1076 | G | T | 3869 | G | T |
| 1325 | C | A | 3880-3881 | TG | AA |
| 2818 | A | T | 3926 | T | G |
| 2857 | T | C | 3932 | T | C |
| 2895 | A | G | | | |
| 2955 | T | C | | | |

Illustrative drought tolerance marker DNA sequences SEQ ID NOs: 10, 11, or 20 can be amplified using the primers indicated in Table 2a as SEQ ID NOs: 28 and 43, 29 and 44, or 30 and 45, respectively, and detected with probes indicated in Table 2a as SEQ ID NOs: 58 and 73, 59 and 74, or 60 and 75, respectively.

Furthermore, SNPs within the csd1 or csd2 gene sequences, like those in Table 2b, can be used to detect and track the inheritance of genotypes associated with drought resistance using the methods described herein. One benefit of using a marker located within a desired gene sequence is a drastic reduction in the possibility that the SNP will become separated from the gene sequence by a recombination event during meiosis.

Example 2. Association Studies

Corn plant drought tolerance phenotypes were scored by denying plants water during either their flowering period or during their grainfill period, or not irrigating them at all throughout their entire growth period in dryland conditions (DL), and then scoring the phenotypic effects on either their anthesis silking interval in days (ASI), 2) their total grain yield in bushels/acre (YLD), growing degree units (GDU), the number of GDU until 50% silking was observed (SLK), harvested grain test weight in pounds/bushel (TWT), harvest moisture content percent (MST), yield:moisture ratio (YM), plant height in centimeters (PHT), ear height in centimeters (EHT), the number of days following pollination until 90% pollen shed (P50D), or the number of barren plants per plot (BARP).

Four independent populations (Table 3) consisting of several hundred proprietary inbred maize lines representative of either North American maize germplasm (populations 1, 2, and 4) or Mexican maize germplasm (population 3) were genotyped with SNP markers and phenotyped for drought tolerance using a combination of standard methods of the art and those described herein.

TABLE 3

Four association analysis studies performed on different populations representative of US and Mexican maize inbred germplasm.

| Study | Treatments | Traits | No. of Individuals | No. of SNP |
|---|---|---|---|---|
| 1 | FL, GF | YLD, MST, TWT, YM, GDU, SLK, ASI, BARP | 892 | 2349 |
| 2 | FL | YLD, MST, YM, TWT, PHT, EHT, ASI, BARP, LFIRE | 1642 | 2442 |
| 3 | FL, GF | YLD, MST, TWT, YM, GDU, SLK, ASI, BARP | 396 | 2184 |
| 4 | DL | YLD, ASI, BARP, EHT, GDU, MST, SLK, P50D | 2048 | 2207 |

SNPs were specifically selected such that they collectively span each chromosome in the maize genome. Each individual in each population was genotyped at each SNP. Loci were eliminated from further analysis in those studies where they were monomorphic in the subject population studied.

Principal Component Analysis (PCA)

In each study, the population structure was evaluated using the PCA method (Price and Patterson et al. 2006) of the genotype covariance matrix and multidimensional scaling analysis (MDS) of the identity-by-state (IBS) matrix from each individual. The PCA of genotypes and classical MDS of the IBS matrix lead to very similar results (Kang and Sul et al. 2010). PCA applies genotype data to infer continuous axes of genetic variation. Intuitively, the axes of variation reduce the data to a small number of dimensions, describing as much variability as possible, and are defined as the top eigenvectors of a covariance matrix between samples.

Structured associations of individual SNP markers with tolerance to drought stress were evaluated by a General Linear Model (GLM) with top (up to 10) eigenvectors added to the model as covariates in four maize populations. The PCAs accounted for >95% of total variation. Genome scan for associations between SNPs and drought tolerance phenotypes was conducted for single marker testing. Proc psmooth/SAS (SAS Institute, 2006) was used for multivariate testing adjustment. An option (adjust=FDR) was adopted that uses false discovery rate to adjust the p-value.

Results

Table 4a lists the significant p-values calculated in the association analysis for markers that map outside of, but are inked to, csd1. Each row provides the maize chromosome where the marker is located, the population that the marker was tested in, the phenotypic trait that was scored, the growing period under which the population was subjected to low water (drought) conditions, the statistical significance (p-value) of the association between the marker and the drought trait, and the estimated effect that the marker polymorphism had on the given trait. For example, SEQ ID NO. 3 was associated with a 0.3 pound/acre increase in test weight in population 1 when that population was denied water during its grainfill period. SEQ NO. 5 was associated with a 9.22 bu/acre decrease in yield when population 1 was denied water during its flowering period.

Table 4b lists the significant p-values calculated in the association analysis for markers that map outside of, but are linked to, csd2. Each row provides the maize chromosome where the marker is located, the population that the marker was tested in, the phenotypic trait that was scored, the growing period under which the population was subjected to low water (drought) conditions, the statistical significance (p-value) of the association between the marker and the drought trait, and the estimated effect that the marker polymorphism had on the given trait. For example, SEQ ID NO. 15 was associated with a 0.05 harvest moisture percent in population 3 when that population was denied water during its grainfill period. SEQ ID NO. 19 was associated with a 0.48 bu/acre decrease in yield when population 4 was denied water in dryland conditions throughout its growth period.

TABLE 4a

Statistical associations of markers flanking, but linked to, csd1 with drought tolerance phenotypes in the maize genome.

| SEQ ID NO. | Chr | Pop | Trait | Period | p-val | Effect |
|---|---|---|---|---|---|---|
| 3 | 4 | 1 | TWT | GF | 0.0001 | 0.30 |
| 4 | 4 | 1 | BARP | FL | 0.0452 | 0.03 |
| 5 | 4 | 1 | BARP | FL | <0.001 | 4.81 |
| 5 | 4 | 1 | YLD | FL | <0.001 | −9.22 |
| 6 | 4 | 1 | BARP | FL | <0.001 | 8.27 |
| 6 | 4 | 1 | YLD | FL | 0.0001 | −18.37 |
| 7 | 4 | 1 | BARP | FL | <0.001 | 8.27 |
| 7 | 4 | 1 | YLD | FL | <0.001 | −15.39 |
| 7 | 4 | 1 | YLD | FL | 0.0003 | 3.74 |
| 7 | 4 | 1 | BARP | FL | <0.001 | −2.07 |
| 8 | 4 | 1 | YLD | FL | 0.0001 | −18.37 |
| 9 | 4 | 3 | EHT | GF | 0.0049 | −0.15 |
| 10 | 4 | 3 | EHT | FL | 0.0001 | −0.34 |
| 11 | 4 | 1 | TWT | FL | <0.001 | −0.41 |
| 12 | 4 | 1 | YLD | FL | 0.0239 | 0.02 |

TABLE 4b

Statistical associations of markers flanking, but linked to csd2 with drought tolerance phenotypes in the maize genome.

| SEQ ID NO. | Chr | Pop | Trait | Period | p-val | Effect |
|---|---|---|---|---|---|---|
| 13 | 10 | 1 | YM | FL | <0.001 | 0.41 |
| 13 | 10 | 1 | BARP | FL | <0.001 | −2.92 |
| 14 | 10 | 1 | MST | GF | 0.0004 | 0.50 |
| 14 | 10 | 3 | TWT | FL | 0.0365 | −0.01 |
| 15 | 10 | 3 | MST | GF | 0.0005 | 0.05 |
| 16 | 10 | 1 | GDU | FL | 0.0000 | 28.14 |
| 16 | 10 | 1 | MST | FL | 0.0000 | −0.36 |
| 16 | 10 | 1 | SLK | FL | 0.0007 | −9.75 |
| 16 | 10 | 1 | GDU | FL | 0.0001 | −8.57 |
| 16 | 10 | 4 | ASI | DL | 0.0174 | −0.61 |
| 16 | 10 | 2 | ASI | DL | 0.0004 | −1.89 |
| 17 | 10 | 1 | GDU | FL | 0.0001 | −8.71 |
| 17 | 10 | 1 | SLK | FL | 0.0002 | −16.98 |
| 17 | 10 | 1 | GDU | FL | 0.0000 | 28.14 |
| 18 | 10 | 1 | SLK | FL | 0.0002 | −16.98 |
| 18 | 10 | 1 | MST | FL | <0.001 | 0.30 |
| 18 | 10 | 1 | SLK | FL | <0.001 | 9.40 |
| 18 | 10 | 1 | GDU | FL | <0.001 | 7.06 |
| 18 | 10 | 4 | ASI | DL | 0.0767 | 0.35 |
| 18 | 10 | 4 | SLK | DL | <0.001 | 2.88 |
| 19 | 10 | 4 | YLD | DL | <0.001 | −0.48 |
| 20 | 10 | 1 | BARP | FL | 0.0139 | −0.07 |
| 20 | 10 | 1 | BARP | FL | 0.0139 | −0.07 |
| 20 | 10 | 1 | MST | FL | <0.001 | 0.36 |
| 20 | 10 | 1 | SLK | FL | <0.001 | 11.72 |
| 20 | 10 | 1 | GDU | FL | <0.001 | 9.93 |
| 20 | 10 | 4 | GDU | DL | <0.001 | 7.28 |

Table 5a lists the significant p-values calculated in the association analysis for markers that map within the csd1 sequence. Each row provides the estimated effect that a polymorphism had on a given trait at the given SNP position within csd1 when population 1 was denied water during a given growing period. For example, SNP position 459 of the csd1 sequence was associated with a 36.81 bu/acre increase in yield in population 1 when those plants were denied water during their flowering period (p-value=0.0092).

TABLE 5a

Statistical associations of markers within csd1 with drought tolerance phenotypes in the maize genome and their estimated effects.

| Locus | SNP Pos | Trait | Period | p-val | Effect |
|---|---|---|---|---|---|
| csd1 | 459 | YLD | FL | 0.0092 | 36.81 |
| csd1 | 466 | YLD | FL | 0.0082 | 33.75 |
| csd1 | 504-506 | YLD | FL | 0.0082 | 33.75 |
| csd1 | 723 | ASI | FL | 0.0059 | 24.38 |
| csd1 | 763 | ASI | FL | 0.0223 | 21.01 |
| csd1 | 947 | ASI | FL | 0.0084 | 24.73 |
| csd1 | 955 | YLD | FL | 0.0442 | 22.38 |
| csd1 | 956 | ASI | FL | 0.0314 | 22.17 |
| csd1 | 956 | YLD | GF | 0.0496 | −9.90 |
| csd1 | 958 | YLD | FL | 0.0442 | 22.38 |
| csd1 | 967 | YLD | FL | 0.0442 | −22.38 |
| csd1 | 1076 | YLD | GF | 0.0268 | 18.07 |
| csd1 | 1325 | ASI | FL | 0.0257 | −21.55 |
| csd1 | 2818 | ASI | FL | 0.0317 | −20.93 |
| csd1 | 2818 | BARP | FL | 0.0164 | −5.73 |
| csd1 | 2818 | YLD | FL | 0.0025 | 20.29 |
| csd1 | 2857 | YLD | FL | 0.0189 | −14.63 |
| csd1 | 2895 | YLD | FL | 0.0126 | 16.71 |
| csd1 | 2955 | BARP | FL | 0.0079 | −5.94 |
| csd1 | 2955 | YLD | FL | 0.0152 | 15.46 |

Table 5b lists the significant p-values calculated in the association analysis for markers that map within the csd2 sequence. Each row provides the estimated effect that a polymorphism had on a given trait at the given SNP position within csd2 when population 1 was denied water during a given growing period. For example, SNP position 3776 of csd2 was associated with a 16.12 bu/acre increase in yield in population 1 when those plants were denied water during their grainfill period (p-value=0.0017).

TABLE 5b

Statistical associations of markers within csd2 with drought tolerance phenotypes in the maize genome and their estimated effects.

| Locus | SNP Pos | Trait | Period | p-val | Effect |
|---|---|---|---|---|---|
| csd2 | 3648 | YLD | GF | 0.0463 | −11.10 |
| csd2 | 3728-3730 | YLD | GF | 0.0182 | 12.75 |
| csd2 | 3756 | YLD | GF | 0.0411 | −26.44 |
| csd2 | 3763 | YLD | GF | 0.0411 | 26.44 |
| csd2 | 3776 | YLD | GF | 0.0017 | 16.12 |
| csd2 | 3799 | YLD | GF | 0.0257 | −23.88 |
| csd2 | 3815 | YLD | GF | 0.0468 | −19.46 |
| csd2 | 3849 | YLD | GF | 0.0005 | 14.28 |
| csd2 | 3852 | YLD | GF | 0.0005 | 14.22 |
| csd2 | 3860 | YLD | GF | 0.0188 | 10.29 |
| csd2 | 3861-3863 | YLD | GF | 0.0233 | 30.60 |
| csd2 | 3869 | YLD | GF | 0.0075 | 12.03 |
| csd2 | 3880-3881 | YLD | GF | 0.0252 | −10.48 |
| csd2 | 3926 | YLD | GF | 0.0233 | −30.60 |
| csd2 | 3932 | YLD | GF | 0.0044 | −14.56 |

The significance level (p-value) was adjusted by multi-point testing based on 5% false discovery rate (FDR). The lower the probability value, the more significant the association between the marker genotype at that locus for the drought tolerance phenotype, i.e., the greater likelihood that the marker genotype is associated with the phenotype. In addition to single marker fitting above, a joint fitting of all markers via LASSO (least absolute shrinkage and selection operator) was also performed. Finally, a set of consensus markers that associated with drought phenotype were selected. A more complete discussion of the derivation of the probability values can be found in the documentation provided with the software. Further descriptions are provided by Sokal and Rolf (1981), Biometry: The Principles and Practices of Statistics in Biological Research, 2nd ed., San Francisco, W. H. Freeman and Co.

Example 3. Detecting Drought Tolerance in a Population of Plants and Monitoring the Introgression of Drought Tolerance Loci from One Plant Line into Another Via MAS A population of corn plants can be phenotyped using any method that gauges the effect of drought conditions on a plant trait, including the methods described in Example 1. The genotypes of the plants in the population at one or more markers that map to the csd1 or csd2 chromosome intervals, or at one or more markers closely linked to one of those three intervals, can also be determined. In one embodiment, statistical associations can then be made between the recorded phenotypes and the genotypes using a variety of methods known in the art, including those described herein.

In one embodiment, genotypes of offspring derived from one or more individuals in the population can be compared to the genotypes of the parents at one or more marker loci linked to csd1 or csd2 genotypes of the parents at those same loci. Individuals that share marker genotypes with the resistant parent at one or more markers can then be selected for advancement in the breeding program. Individuals that do not share marker genotypes with the resistant parent, or individuals that do share marker genotypes with the susceptible parent, can be discarded. This process saves the laborious and time consuming process of phenotyping plants to verify which are resistant or susceptible.

In some embodiments, useful markers comprise any marker that is genetically linked to csd1 or csd2 (SEQ ID NO. 1 and 2, respectively). In other embodiments, useful markers comprise any marker that maps between publically available markers IDP7557 and isu61b. In other embodiments, associations are made between genotypes for one or more SNP markers that map between publically available markers bnlg1028 and rz569a.

Selections and assays may be performed on single loci, or simultaneously on multiple loci. For example, a breeder skilled in the art could base advancement decisions on the genotypes of markers linked to csd1 and genotypes of markers linked to csd2, simultaneously. For instance, a breeder may require that the same plant must exhibit tolerance genotypes at one or more markers linked to csd1 and/or at one or more markers linked to csd2 in order to be advanced. In other embodiments, a single tolerance genotype at only one locus may be sufficient for advancement.

By selecting only those individuals with the resistant genotype for advancement in the breeding program, the frequency of resistant alleles and resistant phenotypes can be more effectively increased in future generations.

The introgression of one or more tolerance loci from a donor line into another is achieved via repeated backcrossing to a recurrent parent accompanied by selection to retain one or more drought tolerance loci from the donor parent. Markers associated with drought tolerance are assayed in progeny and those progeny with one or more drought tolerance markers are selected for advancement. In another aspect, one or more markers can be assayed in the progeny to select for plants with the genotype of the agronomically elite parent. This invention anticipates that trait introgression activities will require more than one generation, wherein progeny are crossed to the recurrent (agronomically elite) parent or selfed. Selections are made based on the presence of one or more drought tolerance markers and can also be made based on recurrent parent genotype, wherein screening is performed on a genetic marker and/or phenotype basis. In another embodiment, markers of this invention can be used in conjunction with other markers, ideally at least one on each chromosome of the corn genome, to track the introgression of drought tolerance loci into elite germplasm. In yet another embodiment, at least 100 SNP markers assorted across the 10 chromosomes of corn will be useful in conjunction with the SNP molecular markers of the present invention to follow the introgression of drought tolerance into elite germplasm. In a preferred embodiment, about three hundred fifty SNP markers, distributed every 5 centimorgans across the 10 chromosomes of the corn genetic linkage map, will be useful in conjunction with the SNP molecular markers of the present invention to follow the introgression of drought tolerance into elite germplasm. In another embodiment, QTLs associated with drought tolerance will be useful in conjunction with SNP molecular markers of the present invention to combine quantitative and qualitative drought tolerance in the same plant. It is within the scope of this invention to utilize the methods and compositions for trait integration of drought tolerance. It is contemplated by the inventors that the present invention will be useful for developing commercial varieties with drought tolerance and an agronomically elite phenotype.

For example, one skilled in the art can use one or more markers linked to csd1 or csd2, for example, those listed herein, to select plants for drought tolerance genotypes arising from the donor while selecting for the recipient genotypes in adjacent chromosome regions. In practice, this reduces the amount of linkage drag from the donor genome that may be associated with undesirable agronomic properties. This backcrossing procedure is implemented at any stage in line development and occurs in conjunction with breeding for superior agronomic characteristics or one or more traits of interest, including transgenic and nontransgenic traits.

Alternatively, a forward breeding approach is employed wherein one or more drought tolerance loci can be monitored for successful introgression following a cross with a susceptible parent with subsequent generations genotyped for one or more drought tolerance loci and for one or more additional traits of interest, including transgenic and non-transgenic traits.

This invention can be used on populations other than those specifically described in this application without altering the methods described herein. Although different parents may have different genotypes at a given marker, the method of using this invention is fundamentally identical. Parents are first phenotyped for drought tolerance, genotyped at each marker, and then those genotypes are used to infer resistant or susceptible phenotypes in progeny derived from those parents, or in any other population where the same genotypes are associated with the same phenotypes.

Example 5. Transforming a Plant with Cloned Csd1 and Csd2 Tolerance Gene Sequences Csd1 or csd2 or both loci from a drought tolerant donor plant can be cloned and used to transform a recipient plant using methods known in the art.

At least one of the cloned resistant loci is integrated into a recombinant DNA construct suitable for plant transformation. In one embodiment, the at least one csd1 or csd2 gene is linked to at least one promoter, such as CaMv35S, or other DNA sequence that modifies expression of the gene, such as an enhancer sequence or polyadenylation signal.

Transgenic plants comprising or derived from plant cells transformed with the csd1 or csd2 loci are then cultured to develop transgenic seeds that can be harvested and used to perpetuate progeny generations of transformed plants expressing the resistant csd1 or csd2 genes transgenically. In one embodiment, either the transgenic csd1 or csd2 gene is expressed in the transformed plants. In another embodiment, the csd1 or csd2 genes are stacked in the same genome and express substantially simultaneously in the same plant.

All patent and non-patent documents cited in this specification are incorporated herein by reference in their entireties, to the same extent as if each individual was specifically and individually indicated to be incorporated by reference. Documents cited herein as being available from the World Wide Web at certain internet addresses are also incorporated herein by reference in their entireties. Certain biological sequences referenced herein by their "NCBI Accession Number" can be accessed through the National Center of Biotechnology Information.

It is intended that all matter contained in the foregoing description or shown in the accompanying drawings shall be interpreted as illustrative rather than limiting. Modifications in arrangement and detail that do not depart from the principles of the invention described herein are considered to fall within the spirit and scope of the appended claims. Thus, the breadth and scope of the present invention should not be limited by any of the above-described exemplary embodiments, but should be defined only in accordance with the following claims appended hereto and their equivalents.

What is claimed is:

1. A method of creating a population of corn plants with enhanced drought tolerance, said method comprising:
   a. providing a first population of corn plants;
   b. detecting the presence of an enhanced drought tolerance allele, wherein said allele is within 5 cM of a nucleotide corresponding to position 3776 of SEQ ID NO. 2 in the first population, and wherein said nucleotide at said position is associated with an enhanced drought tolerance phenotype;
   c. selecting one or more corn plants based on the presence of the enhanced drought tolerance allele from the first population of corn plants; and
   d. producing a population of offspring from the one or more selected corn plants wherein the offspring population exhibits enhanced drought tolerance as compared to the first population.

2. The method of claim 1, wherein said detecting the presence of the enhanced drought tolerance allele comprises detecting a genetic marker within SEQ ID NO. 2.

3. A method of increasing the frequency of a drought tolerance phenotype in a population of corn plants, said method comprising:
   a. providing a first population of corn plants;
   b. detecting the presence of an enhanced drought tolerance allele, wherein said allele is within 5 cM of a nucleotide corresponding to position 3776 of SEQ ID NO. 2 in the first population, and wherein said nucleotide at said position is associated with an enhanced drought tolerance phenotype;
   c. selecting one or more corn plants based on the presence of the enhanced drought tolerance allele from the first population of corn plants; and
   d. producing an offspring population from the one or more selected corn plants such that the drought tolerance phenotype occurs more frequently in the offspring population as compared to the first population.

4. The method of claim 3, wherein the detecting the presence of the enhanced drought tolerance allele comprises detecting a genetic marker within SEQ ID NO. 2.

5. The method of claim 1, wherein said providing a first population of corn plants comprises crossing a corn plant comprising said enhanced drought tolerance allele with a second corn plant of a different genotype lacking said allele.

6. The method of claim 1, wherein the population of corn plants comprises $F_2$-$F_6$ progeny plants.

7. The method of claim 1, wherein said providing a first population of corn plants comprises backcrossing.

8. The method of claim 7, wherein backcrossing comprises marker-assisted selection in at least two generations.

9. The method of claim 8, wherein backcrossing comprises marker-assisted selection in all generations.

10. The method of claim 1, further comprising assaying the selected one or more corn plants comprising said allele or a progeny thereof comprising the allele for said enhanced drought tolerance.

11. The method of claim 3, wherein said providing a first population of corn plants comprises crossing a corn plant comprising at least a first enhanced drought tolerance allele with a second corn plant of a different genotype lacking said allele to produce progeny plants.

12. The method of claim 3, wherein the population of corn plants comprises $F_2$-$F_6$ progeny plants.

13. The method of claim 3, wherein said providing a first population of corn plants comprises backcrossing.

14. The method of claim 13, wherein backcrossing comprises marker-assisted selection in at least two generations.

15. The method of claim 14, wherein backcrossing comprises marker-assisted selection in all generations.

16. The method of claim 3, further comprising assaying the selected one or more corn plants comprising said allele or a progeny thereof comprising the allele for said enhanced drought tolerance.

* * * * *